(12) United States Patent
Bosmans et al.

(10) Patent No.: US 8,334,304 B2
(45) Date of Patent: *Dec. 18, 2012

(54) AMINOSULFONYL SUBSTITUTED 4-(AMINOMETHYL)-PIPERIDINE BENZAMIDES AS 5HT$_4$-ANTAGONISTS

(75) Inventors: Jean-Paul Rene Marie Andre Bosmans, Rijkevorsel (BE); Henricus Jacobus Maria Gijsen, Breda (NL); Laurence Anne Mevellec, Louviers (FR)

(73) Assignee: Janssen Pharmaceutica N.V., Beerse (BE)

( * ) Notice: Subject to any disclaimer, the term of this patent is extended or adjusted under 35 U.S.C. 154(b) by 440 days.

This patent is subject to a terminal disclaimer.

(21) Appl. No.: 12/633,122

(22) Filed: Dec. 8, 2009

(65) Prior Publication Data

US 2010/0087483 A1 Apr. 8, 2010

Related U.S. Application Data

(62) Division of application No. 10/560,300, filed as application No. PCT/EP2004/006280 on Jun. 10, 2004, now Pat. No. 7,652,040.

(30) Foreign Application Priority Data

Jun. 19, 2003 (WO) ................. PCT/EP03/50238

(51) Int. Cl.
*A61K 31/445* (2006.01)
*C07D 405/12* (2006.01)

(52) U.S. Cl. ........................ 514/320; 546/197

(58) Field of Classification Search .................. 514/320; 546/197
See application file for complete search history.

(56) References Cited

U.S. PATENT DOCUMENTS

| | | | |
|---|---|---|---|
| 4,186,135 A | 1/1980 | Thominet et al. | |
| 6,544,997 B1 | 4/2003 | Bosmans et al. | |
| 6,888,027 B2 | 5/2005 | Watkins et al. | |
| 7,635,706 B2 * | 12/2009 | Bosmans et al. | 514/320 |
| 7,652,040 B2 | 1/2010 | Bosmans et al. | |

FOREIGN PATENT DOCUMENTS

| | | |
|---|---|---|
| ES | 2103675 A | 9/1997 |
| WO | WO 9405654 A1 | 3/1994 |
| WO | WO-99/02156 A | 1/1999 |
| WO | WO-00/15636 A | 3/2000 |
| WO | WO-00/37461 A | 6/2000 |

OTHER PUBLICATIONS

Langlois et al. "5-HT4 receptor . . . " J. Med. Chem. v.48(3) p. 319-344 (2003).*
Novartis Pharma "Irritable Bowel . . . " Tech. Services Bus. Brief. p. 1-5 (2004).*
Baudoin et al. "Preparation of 4-[(imidazolylmethyl . . . " CA 134:163037 (2001).
Chavatte et al. "Three dimensional . . . " J. Med. Chem. v.14, p. 3223-3230 (2001).
Gorrod et al., "The Metabolism of N-Ethyl-N-methylaniline by Rabbit Liver Microsomes: The Measurement of Metabolites by Gas-liquid Chromatography," Xenobiotica, Jan. 1975, vol. 5, No. 8, pp. 453-463.
Hayashi et al. "Cyclic amines and . . . " CA 146:455250 (2007).
Lima et al. "bioisosterism: a useful strategy for . . . " Current medicinal che. V.12, p. 23-49 (2005).
Penning et al. "synthesis and biological . . . " J. Med. Chem, v.40, p. 1347-1365 (1997).
Search Report for International Application No. PCT/EP/2004/006280, Jun. 1, 2005, 5 pages.
Supuran et al. "Cox-2 selective . . . " Mini-rev. Med. Chem. v.4, p. 625-632 (2004).
VanDaele et al. "Diamethylbenzofuran . . . " CA 127::331398 (1997).

\* cited by examiner

*Primary Examiner* — Celia Chang
(74) *Attorney, Agent, or Firm* — Woodcock Washburn LLP

(57) ABSTRACT

The present invention is concerned with novel compounds of formula (I) having 5HT$_4$-antagonistic properties. The invention further relates to methods for preparing such novel compounds, pharmaceutical compositions comprising said novel compounds as well as the use as a medicine of said compounds.

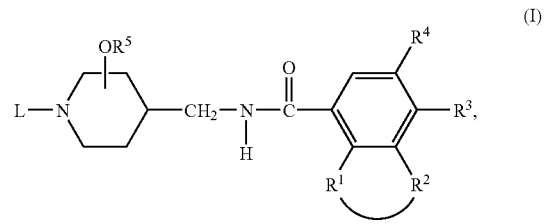

8 Claims, No Drawings

AMINOSULFONYL SUBSTITUTED 4-(AMINOMETHYL)-PIPERIDINE BENZAMIDES AS 5HT$_4$-ANTAGONISTS

This application is a divisional of U.S. application Ser. No. 10/560,300, filed Dec. 12, 2005, which is the National Stage Entry of International Application No. PCT/EP04/06280, filed Jun. 10, 2004, which claims the benefit of European Patent Application No. 03/50238, filed Jun. 19, 2003.

The present invention is concerned with novel compounds of formula (I) having 5HT$_4$-antagonistic properties. The invention further relates to methods for preparing such novel compounds, pharmaceutical compositions comprising said novel compounds as well as the use as a medicine of said compounds.

WO-00/37461 discloses bicyclic benzamides of 3- or 4-substituted 4-(aminomethyl)-piperidine derivatives having 5HT$_4$-antagonistic properties.

The compounds of the present invention differ structurally from the cited art-known compounds by the presence of a different L radical moiety.

Unexpectedly, the present compounds of formula (I) have improved metabolic stability properties compared with the compounds disclosed in WO-00/37461.

The present invention concerns compounds of formula (I)

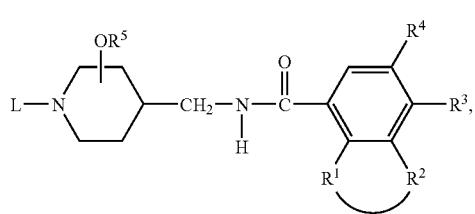

a stereochemically isomeric form thereof, an N-oxide form thereof, or a pharmaceutically acceptable acid or base addition salt thereof,
wherein
—R$^1$—R$^2$— is a bivalent radical of formula

| —O—CH$_2$—O— | (a-1), |
| —O—CH$_2$—CH$_2$— | (a-2), |
| —O—CH$_2$—CH$_2$—O— | (a-3), |
| —O—CH$_2$—CH$_2$—CH$_2$— | (a-4), |
| —O—CH$_2$—CH$_2$—CH$_2$—O— | (a-5), |
| —O—CH$_2$—CH$_2$—CH$_2$—CH$_2$— | (a-6), |
| —O—CH$_2$—CH$_2$—CH$_2$—CH$_2$—O— | (a-7), |
| —O—CH$_2$—CH$_2$—CH$_2$—CH$_2$—CH$_2$— | (a-8), | wherein in said bivalent radicals optionally one or two hydrogen atoms on the same or a different carbon atom may be replaced by C$_{1-6}$alkyl or hydroxy,
R$^3$ is hydrogen, halo, C$_{1-6}$alkyl or C$_{1-6}$alkyloxy;
R$^4$ is hydrogen, halo, C$_{1-6}$alkyl; C$_{1-6}$alkyl substituted with cyano, or C$_{1-6}$alkyloxy; C$_{1-6}$alkyloxy; cyano; amino or mono or di(C$_{1-6}$alkyl)amino;
R$^5$ is hydrogen or C$_{1-6}$alkyl, and the —OR$^5$ radical is situated at the 3- or 4-position of the piperidine moiety;

L is a radical of formula

| -Alk-R$^6$ | (b-1), |
| -Alk-X—R$^7$ | (b-2), |
| -Alk-Y—C(=O)—R$^9$ | (b-3), |
| -Alk-C(=O)—NH—C(=O)—R$^{11}$ | (b-4), |
| -Alk-C(=O)—NH—SO$_2$—R$^{11}$ | (b-5), |
| -Alk-SO$_2$—NH—C(=O)—R$^{11}$ | (b-6), |
| -Alk-SO$_2$—NH—SO$_2$—R$^{11}$ | (b-7), | wherein each Alk is C$_{1-12}$alkanediyl; and
R$^6$ is aminosulfonyl optionally substituted with C$_{1-4}$alkyl, C$_{3-6}$cycloalkyl or phenyl;
R$^7$ is C$_{1-6}$alkylsulfonyl;
X is NR$^8$; said R$^8$ being C$_{1-6}$alkyl;
R$^9$ is C$_{1-6}$alkylsulfonylamino;
Y is a O, S, or NR$^{10}$ wherein R$^{10}$ is hydrogen or C$_{1-6}$alkyl; and
R$^{11}$ is C$_{1-6}$alkyl or phenyl.

As used in the foregoing definitions halo is generic to fluoro, chloro, bromo and iodo; C$_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like; C$_{1-6}$alkyl is meant to include C$_{1-4}$alkyl and the higher homologues thereof having 5 or 6 carbon atoms, such as, for example, 2-methyl-butyl, pentyl, hexyl and the like; C$_{3-6}$cycloalkyl is generic to cyclopropyl, cyclobutyl, cyclopentyl and cyclohexyl; C$_{1-12}$alkanediyl defines bivalent straight or branched chain hydrocarbon radicals containing from 1 to 12 carbon atoms such as, for example, methanediyl, 1,2-ethanediyl, 1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl and the branched isomers thereof. C$_{1-4}$alkanediyl defines bivalent straight or branched chain hydrocarbon radicals containing from 1 to 4 carbon atoms such as, for example, methanediyl, 1,2-ethanediyl, 1,3-propanediyl, and 1,4-butanediyl.

The term "aminosulfonyl" refers to a radical having formula

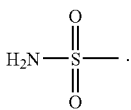

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

Some of the compounds of formula (I) may also exist in their tautomeric form. Such forms although not explicitly indicated in the above formula are intended to be included within the scope of the present invention.

The N-oxide forms of the compounds of formula (I), which may be prepared in art-known manners, are meant to comprise those compounds of formula (I) wherein one or several nitrogen atoms are oxidized to the N-oxide. Particularly those N-oxides are envisaged wherein the piperidine-nitrogen is N-oxidized.

A group of interesting compounds consists of those compounds of formula (I) wherein one or more of the following restrictions apply:
a) —$R^1$—$R^2$— is a radical of formula (a-3); and/or
b) —$R^1$—$R^2$— is a radical of formula (a-5); and/or
c) $R^3$ is hydrogen, halo, methyl, or methoxy; and/or
d) $R^4$ is hydrogen, halo, methyl, cyano, amino or $C_{1-4}$alkylamino; and/or
e) $R^4$ is fluoro; and/or
f) $R^5$ is hydrogen or methyl, and the —$OR^5$ radical is situated at the 3- or 4-position of the piperidine ring; and/or
g) $R^5$ is hydrogen or methyl, and the —$OR^5$ radical is situated at the 3-position of the piperidine ring; and/or
h) $R^5$ is hydrogen, and the —$OR^5$ radical is situated at the 4-position of the piperidine ring; and/or
i) the —$OR^5$ radical, wherein $R^5$ is hydrogen or methyl, is situated at the 3-position of the piperidine ring and is in the trans position in relation to the methylene on the 4-position of the piperidine moiety; and/or
j) the —$OR^5$ radical, wherein $R^5$ is hydrogen or methyl, is situated at the 3-position of the piperidine ring and is in the trans position in relation to the methylene on the 4-position of the piperidine moiety and the absolute configuration of said piperidine moiety is (3S,4S); and/or
k) L is a radical of formula (b-1) wherein Alk is $C_{1-4}$alkanediyl, and $R^6$ aminosulfonyl or aminosulfonyl substituted with $C_{1-4}$alkyl or phenyl; or
L is a radical (b-5) wherein Alk is $C_{1-4}$alkanediyl, and $R^{11}$ is $C_{1-4}$alkyl; or
L is a radical (b-7) wherein Alk is $C_{1-4}$alkanediyl, and $R^{11}$ is $C_{1-4}$alkyl.

Other interesting compounds are those compounds of formula (I) wherein
—$R^1$—$R^2$— is a bivalent radical of formula

—O—CH$_2$—CH$_2$—O— (a-3),

—O—CH$_2$—CH$_2$—CH$_2$—O— (a-5), $R^3$ is hydrogen, halo, $C_{1-6}$alkyl or $C_{1-6}$alkyloxy;
$R^4$ is hydrogen, halo, $C_{1-6}$alkyl; cyano; amino or mono or di($C_{1-6}$alkyl)amino;
$R^5$ is hydrogen or $C_{1-6}$alkyl, and the —$OR^5$ radical is situated at the 3- or 4-position of the piperidine moiety;
L is a radical of formula

-Alk-$R^6$ (b-1),

-Alk-C(=O)—NH—SO$_2$—$R^{11}$ (b-5),

-Alk-SO$_2$—NH—SO$_2$—$R^{11}$ (b-7), wherein each Alk is $C_{1-12}$alkanediyl; and
$R^6$ is aminosulfonyl optionally substituted with $C_{1-4}$alkyl or phenyl;
$R^{11}$ is $C_{1-6}$alkyl.

Particular compounds are those compounds of formula (I) wherein the —$OR^5$ radical, preferably representing hydroxy or methoxy, is situated at the 3-position of the piperidine moiety having the trans configuration, i.e. the —$OR^5$ radical is in the trans position in relation to the methylene on the piperidine moiety.

More particular compounds are those compounds of formula (I) wherein the bivalent radical —$R^1$—$R^2$— is a radical of formula (a-3) or (a-5), the —$OR^5$ radical represents hydroxy and is situated at the 3-position of the piperidine moiety having the (3S-trans) configuration which corresponds to absolute (3S,4S) configuration of said piperidine moiety.

Preferred compounds are those more particular compounds wherein L is a radical of formula (b-1) wherein Alk is $C_{1-4}$alkanediyl, and $R^6$ aminosulfonyl or aminosulfonyl substituted with $C_{1-4}$alkyl or phenyl.

Other preferred compounds are those more particular compounds wherein L is a radical (b-5) wherein Alk is $C_{1-4}$alkanediyl, and $R^{11}$ is $C_{1-4}$alkyl.

Yet other preferred compounds are those more particular compounds wherein L is a radical (b-7) wherein Alk is $C_{1-4}$alkanediyl, and $R^{11}$ is $C_{1-4}$alkyl.

The compounds of formula (I) can be prepared by reacting an intermediate of formula (II) with an carboxylic acid derivative of formula (III) or, optionally a reactive functional derivative thereof, such as, e.g. carbonyl imidazole derivatives, acyl halides or mixed anhydrides. Said amide-bond formation may be performed by stirring the reactants in an appropriate solvent, optionally in the presence of a base, such as triethylamine.

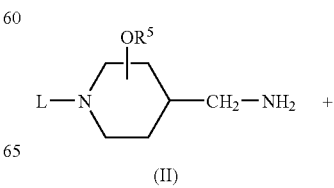
(II)

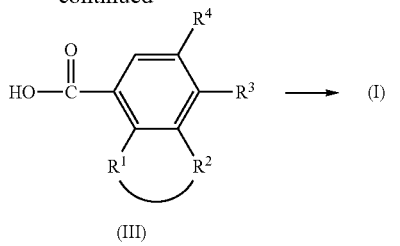

Also compounds of formula (I) can generally be prepared by N-alkylating an intermediate of formula (V) with an intermediate of formula (IV), wherein W is an appropriate leaving group such as, for example, halo, e.g. fluoro, chloro, bromo, iodo, or in some instances W may also be a sulfonyloxy group, e.g. methanesulfonyloxy, benzenesulfonyloxy, trifluoromethanesulfonyloxy and the like reactive leaving groups. The reaction can be performed in a reaction-inert solvent such as, for example, acetonitrile, 2-pentanol, isobutanol, dimethyl acetamide or DMF, and optionally in the presence of a suitable base such as, for example, sodium carbonate, potassium carbonate, N-methylpyrrolidone or triethylamine. Stirring may enhance the rate of the reaction. The reaction may conveniently be carried out at a temperature ranging between room temperature and the reflux temperature of the reaction mixture.

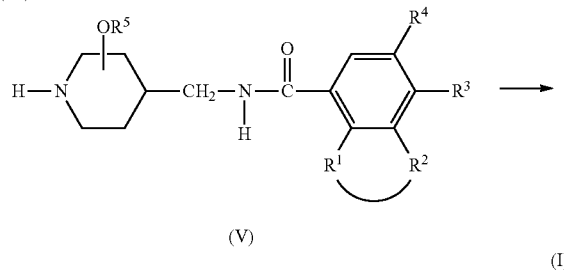

Alternatively, compounds of formula (I) can also be prepared by reductively N-alkylating an intermediate of formula (V) with an intermediate of formula L'=O (VI), wherein L'=O represents a derivative of formula L-H wherein two geminal hydrogen atoms are replaced by oxygen, following art-known reductive N-alkylation procedures.

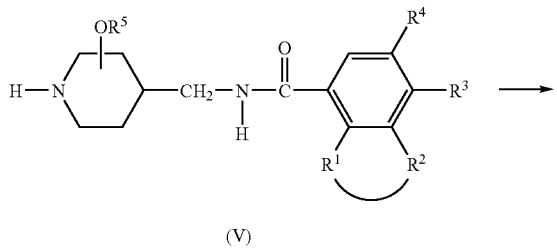

Said reductive N-alkylation can be performed in a reaction-inert solvent such as, for example, dichloromethane, ethanol, toluene or a mixture thereof, and in the presence of a reducing agent such as, for example, a borohydride, e.g. sodium borohydride, sodium cyanoborohydride or triacetoxy borohydride. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. To enhance the rate of the reaction, the temperature may be elevated in a range between room temperature and the reflux temperature of the reaction mixture and optionally the pressure of the hydrogen gas may be raised.

Intermediates of formula (V) can be prepared by reacting an intermediate of formula (VII), wherein PG represents an appropriate art-known protective group, such as for example a tert-butoxycarbonyl or a benzyl group or a photoremovable group, with an acid of formula (III), or an appropriate reactive functional derivative thereof, such as for example carbonyl imidazole derivatives, and subsequent deprotection of the thus formed intermediate, i.e. removal of PG by art-known methods.

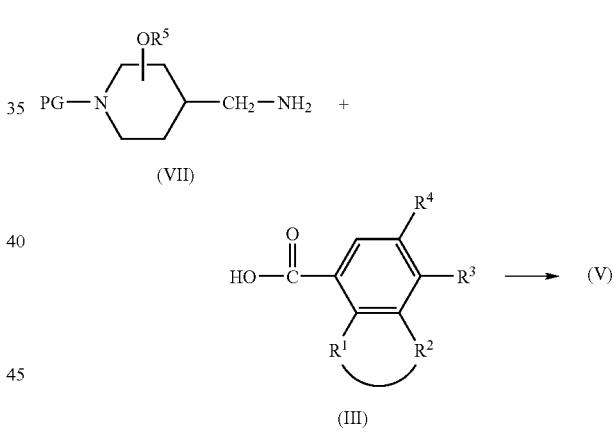

Compounds of formula (I-a), defined as compounds of formula (I) wherein $R^3$ is hydrogen and $R^4$ is amino, can generally be prepared N-alkylating an intermediate of formula (II) with an carboxylic acid derivative of formula (III-a). Said N-alkylation reaction may be performed by stirring the reactants in an appropriate solvent, optionally in the presence of a base, such as potassium carbonate or triethylamine. The N-alkylation reaction is then followed by a hydrogenation procedures using a suitable catalyst such as palladium-on-carbon.

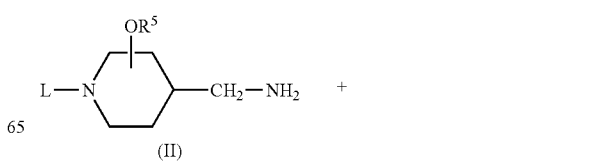

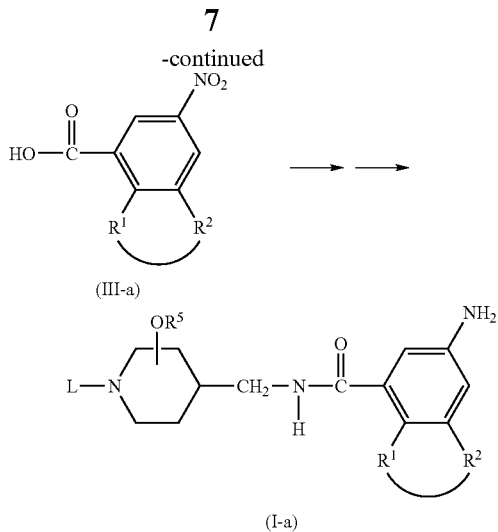

The compounds of formula (I) may further be prepared by converting compounds of formula (I) into each other according to art-known group transformation reactions.

The starting materials and some of the intermediates are known compounds and are commercially available or may be prepared according to conventional reaction procedures generally known in the art. For example, intermediates of formula (II) of (VII) can be prepared according to the methodologies described in WO-99/02156 or WO-00/37461.

Intermediates of formula (VI) can be prepared according to the general methodology described in WO-99/02156 or WO-00/37461 for the therein described intermediates of formula (VIII).

The compounds of formula (I) as prepared in the hereinabove described processes may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the N-oxide forms, the pharmaceutically acceptable acid or base addition salts and stereoisomeric forms thereof possess $5HT_4$-antagonistic properties as described in Example C.1.

Furthermore the compounds of formula (I) have shown improved metabolic stability as described in Example C.2. These advantageous metabolic stability properties result in a reduced risk of drug-drug interaction on the level of cytochrome P450 enzymes such as e.g. CYP1A2, CYP3A4, CYP2D6, CYP2C9 and CYP2C19 and therefore the present compounds have an improved drug safety profile. Furthermore these advantageous metabolic stability properties may allow for a once daily administration of the compounds of formula (I) instead of the usual administration of the active ingredient on a regimen of between two or four intakes per day thereby giving more patient compliance.

In view of the $5HT_4$-antagonistic properties of the compounds of the present invention, the subject compounds may generally be used in the treatment or prophylaxis of gastrointestinal conditions such as hypermotility, irritable bowel syndrome (IBS), constipation- or diarrhea-predominant IBS, pain- and non-pain-predominant IBS, bowel hypersensitivity, and the reduction of pain associated with gastrointestinal hypersensitivity and/or hyperactivity.

It is also believed that the compounds of formula (I) are useful in the prevention or prophylaxis of a disturbed, hampered or impaired gastric accommodation such as dyspepsia. Dyspeptic symptoms are for example epigastric pressure, a lack of appetite, feeling of fullness, early satiety, nausea, vomiting, bloating and gaseous eructation.

The compounds of formula (I) may also be of use in the treatment of other $5HT_4$-related disorders such as boulimia and hyperphagia.

In view of the utility of the compounds of formula (I), it follows that the present invention also provides a method of treating warm-blooded animals, including humans, (generally called herein patients) suffering from gastrointestinal conditions such as irritable bowel syndrome (IBS). Consequently a method of treatment is provided for relieving patients suffering from conditions such as hypermotility, irritable bowel syndrome (IBS), constipation- or diarrhea-predominant IBS, pain- and non-pain-predominant IBS, bowel hypersensitivity, and the reduction of pain associated with gastrointestinal hypersensitivity and/or hyperactivity.

The compounds of formula (I) may also be of potential use in other gastrointestinal disorders, such as those associated with upper gut motility. In particular, they are of potential use in the treatment of gastric symptoms of gastro-oesophageal reflux disease, such as heartburn (including episodic heartburn, nocturnal heartburn, and meal-induced heartburn).

Furthermore, the $5HT_4$-antagonistic compounds of formula (I) may also be of potential use in the treatment or prophylaxis of bladder hypersensitivity, overactive bladder, lower urinary tract symptoms, benign prostatic hypertrophy (BPH), prostatis, detrusor hyperreflexia, outlet obstruction, urinary frequency, nocturia, urinary urgency, pelvic hypersensitivity, urge incontinence, urethritis, prostatodynia, cystitis, idiophatic bladder hypersensitivity, urinary incontinence or urinary incontinence associated with irritable bowel syndrome. In this respect, it may be advantageous to combine the $5HT_4$-antagonistic compounds of formula (I) with an alpha-adrenoceptor antagonist such as alfuzosin, indoramin, tamsulosin, doxazosin, terazosin, abanoquil, or prazosin in order to obtain pharmaceutical compositions comprising such an alpha-adrenoceptor antagonist, and a 5-$HT_4$-receptor antagonist of formula (I).

Hence, the present invention provides compounds of formula (I) for use as a medicine, and in particular the use of compounds of formula (I) for the manufacture of a medicine for treating gastrointestinal conditions such as hypermotility, IBS, constipation- or diarrhea-predominant IBS, pain- and non-pain predominant IBS, bowel hyper-sensitivity, and the reduction of pain associated with gastrointestinal hypersensitivity and/or hyperactivity. Both prophylactic and therapeutic treatment are envisaged.

In view of the $5HT_4$-antagonistic properties of the compounds of the present invention, the subject compounds may also be of use in treating or preventing $5HT_4$-related CNS disorders in a human. In particular, the compounds of formula (I) can be used to treat a variety of CNS disorders including but not limited to drug substance abuse, cognitive disorders such as Alzheimer's disease, senile dementia; behavioral disorders such as schizophrenia, mania, obsessive-compulsive disorder and psychoactive substance use disorders; mood disorders such as depression, bipolar affective disorder, anxiety and panic disorder; disorders of control of autonomic function such as hypertension and sleep disorders; obsessive/compulsive disorders including anorexia and bulimia, and neuropsychiatric disorders, such as Gilles de la Tourette's syndrome, and Huntington's disease.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions may take the form of solid dose forms, for example, tablets (both swallowable-only and chewable forms), capsules or gelcaps, prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means, optionally with pharmaceutically acceptable additives such as suspending agents (e.g. sorbitol syrup, methylcellulose, hydroxypropyl methylcellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

Pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations stronger flavours may be required such as Caramel Chocolate flavour, Mint Cool flavour, Fantasy flavour and the like pharmaceutically acceptable strong flavours. Each flavour may be present in the final composition in a concentration ranging from 0.05% to 1% (w/v). Combinations of said strong flavours are advantageously used. Preferably a flavour is used that does not undergo any change or loss of taste and colour under the acidic conditions of the formulation.

The formulations of the present invention may optionally include an anti-flatulent, such as simethicone, alpha-D-galactosidase and the like.

The compounds of the invention may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as isotonizing, suspending, stabilising and/or dispersing agents. Alternatively, the active ingredient may be in powder form for constitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glycerides.

For intranasal administration the compounds of the invention may be used, for example, as a liquid spray, as a powder or in the form of drops.

In general it is contemplated that a therapeutically effective amount would be from about 0.0001 mg/kg to about 1 mg/kg body weight, preferably from about 0.001 mg/kg to about 0.5 mg/kg body weight.

EXPERIMENTAL PART

In the procedures described hereinafter the following abbreviations were used: "ACN" stands for acetonitrile; "THF", which stands for tetrahydrofuran; "DCM" stands for dichloromethane; "DIPE" stands for diisopropylether; "EtOAc" stands for ethyl acetate; "NH$_4$OAc" stands for ammonium acetate; "MIK" stands for methyl isobutyl ketone, "DMF" stands for dimethylformamide, "DMA" stands for dimethylacetamide. For some chemicals the chemical formula was used, e.g. NaOH for sodium hydroxide, Na$_2$CO$_3$ for sodium carbonate, K$_2$CO$_3$ for potassium carbonate, NH$_3$ for ammonia, CuO for copper(II)oxide, CH$_2$Cl$_2$ for dichloromethane, CH$_3$OH for methanol, HCl for hydrochloric acid, and KOH for potassium hydroxide, NaBF$_4$ for sodium tetrafluoro-borate.

Chiralcel AD is a chiral stationary phase column material purchased from Daicel Chemical Industries, LTd, in Japan.

A. Preparation of the Intermediates

Example A.1 a) Preparation of

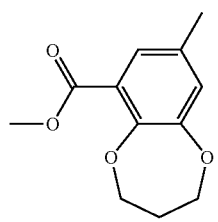

intermediate (1)

A mixture of methyl 2,3-dihydroxy-5-methylbenzoate (0.198 mol), 1,3-dibromopropane (0.198 mol) and K$_2$CO$_3$ (0.396 mol) in 2-propanone (360 ml) was stirred and refluxed for 6 hours, then cooled and the solvent was evaporated. The mixture was poured out into ice water and filtered. The filtrate was extracted with ethyl acetate. The organic layer was separated, dried, filtered, the solvent was evaporated and purified by column chromatography over silica gel (eluent: cyclohexane/ethyl acetate 80/20 to 70/30), yielding intermediate (1).

b) Preparation of

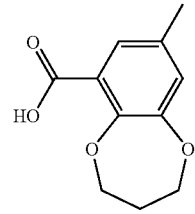

intermediate (2)

A mixture of intermediate (1) (0.1129 mol) in a mixture of a NaOH solution 2N (370 ml) and THF (370 ml) was stirred at room temperature for 15 hours. THF was evaporated and the mixture was acidified with HCl 12N. The precipitate was filtered, washed with water and dried, yielding 21.9 g of intermediate (2) (mp. 74° C.).

Example A.2 a) Preparation of

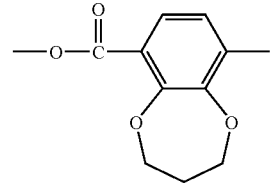

intermediate (3)

A mixture of 2,3-dihydroxy-4-methyl-benzoic acid methylester (1.2 mol), 1,3-dibromo-propane (152 ml) and K$_2$CO$_3$ (380 g) in 2-propanone (2500 ml) was stirred and refluxed for 20 hours. The reaction mixture was cooled, filtered and the filtrate was evaporated, yielding 300 g of intermediate (3).

b) Preparation of

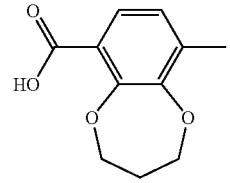

intermediate (4)

A mixture of intermediate (3) (1.12 mol) in NaOH (2 M) (1800 ml) and THF (500 ml) was stirred and refluxed for 3 hours. The reaction mixture was cooled and the organic solvent was evaporated. The aqueous concentrate was acidified with HCl and the resulting precipitate was filtered off, washed with water, and dried, yielding 403 g of intermediate (4).

Example A.3 a) Preparation of

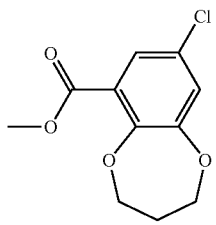

intermediate (5)

A mixture of 5-chloro-2,3-dihydroxy-benzoic acid methyl ester (0.3 mol), 1,3-dibromopropane (0.42 mol) and $K_2CO_3$ (0.66 mol) in 2-propanone (500 ml) was stirred and refluxed for 20 hours, then filtered hot and the filtrate was evaporated. The residue was purified by column chromatography over silica gel (eluent: DCM). The desired fractions were collected and the solvent was evaporated. Toluene was added and azeotroped on the rotary evaporator, yielding 69 g of methyl 8-chloro-3,4-dihydro-2H-1,5-benzodioxepin-6-carboxylate (intermediate 5).

b) Preparation of

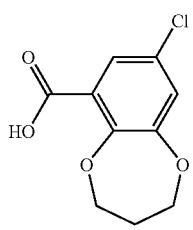

intermediate (6)

A mixture of intermediate (5) (0.25 mol) and KOH (1 mol) in water (650 ml) was stirred and refluxed for 2 hours. The reaction mixture was cooled, acidified with HCl, the resulting precipitate was filtered off, washed with water, and dried, yielding 48 g of 8-chloro-3,4-dihydro-2H-1,5-benzodioxepin-6-carboxylic acid (intermediate 6).

Example A.4 a) Preparation of

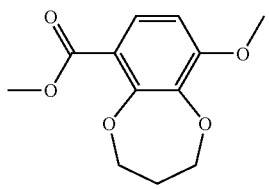

intermediate (7)

A mixture of 2,3-dihydroxy-4-methoxy benzoic acid methyl ester (0.45 mol), 1,3-dibromopropane (0.72 mol), $K_2CO_3$ (155 g) and CuO (3.6 g) in DMF (2500 ml) was stirred at 120° C. to 130° C. for 7 hours, cooled and filtered. The solvent was evaporated. HCl (aqueous solution of 0.5 N, 1000 ml)) was added. The mixture was extracted twice with DCM (750 ml). The organic layer was separated, dried, filtered and the solvent was evaporated. The residue was purified by column chromatography over silica gel (eluent: hexane/ethyl acetate/DCM 70/30/15). The pure fractions were collected and the solvent was evaporated. The residue was crystallized from DIPE, yielding methyl 3,4-dihydro-9-methoxy-2H-1,5-benzodioxepin-6-carboxylate (intermediate 7).

b) Preparation of

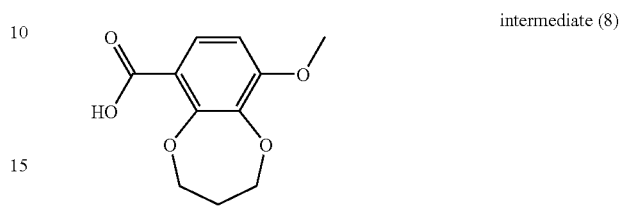

intermediate (8)

A NaOH solution (500 ml, 2N) was added to a solution of intermediate (7) in THF (250 ml). The mixture was stirred at room temperature overnight. The solvent was evaporated partially. The residue was extracted with DCM. The mixture was separated into its layers. The aqueous layer was acidified with a concentrated HCl solution until pH=1 to 2. The solid was filtered off, washed with water and dried, yielding 35.5 g of 9-methoxy-3,4-dihydro-2H-1,5-benzodioxepin-6-carboxylic acid (intermediate 8).

Example A.5 a) Preparation of

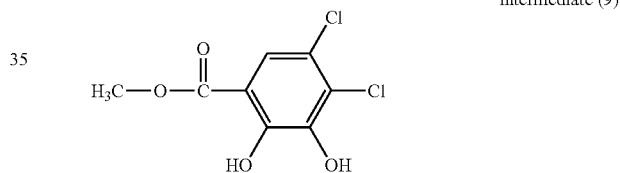

intermediate (9)

A mixture of 5-chloro-2,3-dihydroxy benzoic acid methyl ester (0.49 mol), in acetic acid (2000 ml) was stirred and refluxed. A solution of N-chlorosuccinimide (0.49 mol) in acetic acid (600 ml) was added dropwise at reflux. The reaction mixture was stirred and refluxed for 30 minutes. Extra solution of N-chlorosuccinimide (0.075 mol) in acetic acid (100 ml) was added dropwise at reflux. The reaction mixture was stirred and refluxed for 30 minutes, then cooled and poured out into water (500 ml). The residue was extracted with toluene (3 times). The separated organic layer was washed with water, dried, and evaporated. The residue was crystallized from DIPE and petroleumether, yielding 70 g of intermediate (9).

b) Preparation of

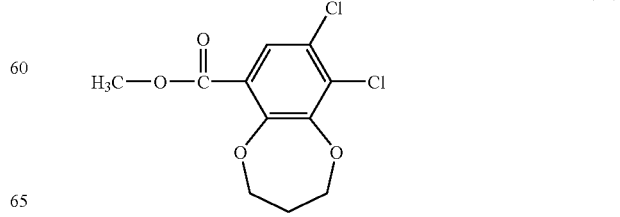

intermediate (10)

A mixture of intermediate (9) (0.3 mol), 1,3-dibromopropane (0.35 mol) and K$_2$CO$_3$ (0.7 mol) in 2-propanone (1000 ml) was stirred and refluxed for 30 hours. The reaction mixture was cooled, diluted with water (2000 ml) and extracted twice with DCM. The separated organic layer was washed with water, dried, and the solvent was evaporated. The residue was crystallized from DIPE and petroleumbenzine, yielding 55 g of intermediate (10).

c) Preparation of

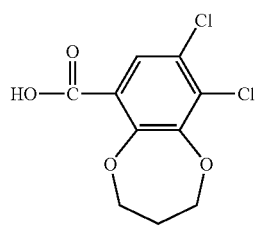

intermediate (11)

A mixture of intermediate (10) (0.2 mol) and KOH (1 mol) in water (1000 ml) was stirred and refluxed for 90 minutes. The reaction mixture was cooled, acidified with HCl and the resulting precipitate was filtered off, washed with water, and dried, yielding 46 g of intermediate (11).

Example A.6 a) Preparation of

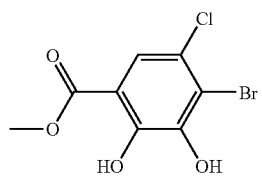

intermediate (12)

A mixture of 5-chloro-2,3-dihydroxy benzoic acid methyl ester (0.1 mol) in acetic acid (250 ml) and N-bromosuccinimide (0.11 mol) was stirred and refluxed for 4 hours. The reaction mixture was cooled and poured out into water (500 ml). The precipitate was filtered and dried, yielding 23 g of intermediate (12).

b) Preparation of

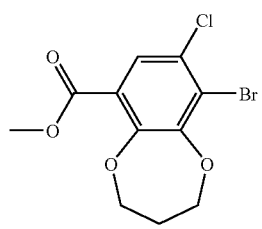

intermediate (13)

A mixture of intermediate (12) (0.7 mol), 1,3-dibromopropane (0.94 mol) and K$_2$CO$_3$ (1.55 mol) in 2-propanone (1300 ml) was stirred and refluxed for 20 hours. The reaction mixture was cooled, filtered and the solvent was evaporated. The residue was solidified in petroleumether, filtered and dried, yielding 240 g of intermediate (13).

c) Preparation of

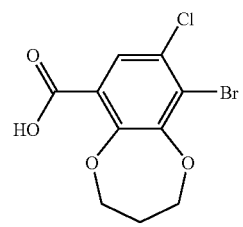

intermediate (14)

A mixture of intermediate (13) (0.053 mol) and KOH (0.2 mol) in water (160 ml) was stirred and refluxed for 90 minutes. The reaction mixture was cooled and the aqueous layer was extracted with DCM. The aqueous layer was acidified with HCl and the resulting precipitate was filtered off, washed with water, and dried, yielding 13 g of intermediate (14).

Example A.7 a) Preparation of

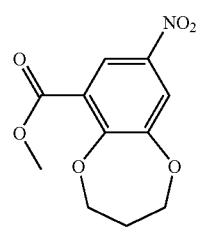

intermediate (15)

A mixture of 5-nitro-2,3-dihydroxybenzoic acid methylester (0.3 mol), K$_2$CO$_3$ (0.66 mol), 1,3-dibromopropane (0.42 mol) and tetra-n-butylammonium bromide (4.5 g) in 2-propanone (900 ml) and DMA (600 ml) was stirred and refluxed for 30 hours. The reaction mixture was stirred for two days at room temperature and then filtered. The solvent was evaporated and the residue was partitioned between water and DCM. The separated organic layer was dried, filtered and concentrated. The residue was suspended in DIPE, filtered, dried and purified by column chromatography over silica gel (eluent: CH$_2$Cl$_2$/CH$_3$OH 98/2), yielding 33.5 g of intermediate (15).

b) Preparation of

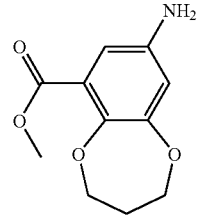

intermediate (16)

A mixture of intermediate (15) (0.11 mol) in THF (250 ml) was hydrogenated with palladium-on-carbon 10% (3 g) as a catalyst in the presence of a thiophene-solution (1 ml). After uptake of hydrogen (3 equivalents), the catalyst was filtered off over dicalite and the filtrate was concentrated, yielding 24.7 g of intermediate (16).

c) Preparation of

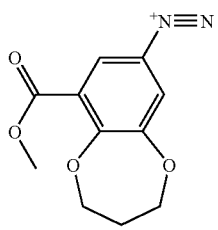
intermediate (17)

Intermediate (16) (0.0448 mol) was added portionwise at 5° C. to a mixture of concentrated HCl (10 ml) in water (10 ml). The mixture was brought to 0° C. A solution of NaNO$_2$ (0.048 mol) in water (10 ml) was added dropwise at 0° C. The mixture was stirred at a temperature between 0° C. and 5° C. for 1 hour, then filtered. The filtrate was cooled to 0° C., then added to a solution of NaBF$_4$ (0.076 mol) in water (20 ml). The mixture was stirred at 0° C. for 30 minutes. The precipitate was filtered, washed with a minimum of water, then with diethyl ether/water (50/50), then with diethyl ether and dried at room temperature under vacuo, yielding 12.10 g of intermediate (17).

d) Preparation of

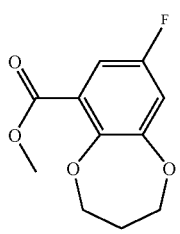
intermediate (18)

A mixture of intermediate (17) (0.0387 mol) and sodium fluoride (0.1549 mol) in toluene (120 ml) was stirred and refluxed overnight, then brought to room temperature. The precipitate was filtered. The filtrate was washed with toluene and evaporated till dryness. The residue was taken up in DCM. The solvent was evaporated till dryness. The residue was purified by column chromatography over silica gel (eluent: DCM), yielding 2.8 g of intermediate (18).

e) Preparation of

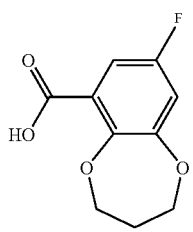
intermediate (19)

A mixture of intermediate (18) (0.0124 mol) in a NaOH solution (2N, 25 ml) and THF (25 ml) was stirred at room temperature overnight. THF was evaporated and ethyl acetate was added. The mixture was extracted with ethyl acetate, then acidified with HCl till pH 2 was obtained. The precipitate was filtered, washed with water, then with diethyl ether and dried, yielding 2.16 g of intermediate (19).

Example A.8 a) Preparation of

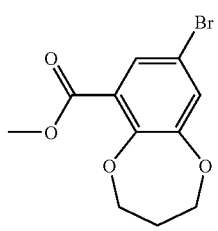
intermediate (20)

A mixture of 5-bromo-2,3-dihydroxy-benzoic acid methyl ester (0.397 mol) and K$_2$CO$_3$ (0.87 mol) in 1,3-dibromopropane (49 ml) and 2-propanone (1000 ml) was stirred and refluxed for 22 hours, then the reaction mixture was cooled, filtered over dicalite and the solvent was evaporated. The residue was partitioned between NaHCO$_3$ (5%, aq.) and DCM. The organic layer was separated, dried, filtered over dicalite and the solvent was evaporated, yielding 112 g intermediate (20).

b) Preparation of

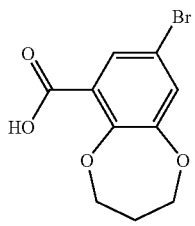
intermediate (21)

A mixture of intermediate (20) (0.14 mol) in THF (200 ml) and NaOH solution 2N (300 ml) was stirred at 30-60° C. for 4 hours, then the organic solvent was evaporated and the aqueous concentrate was cooled on ice and extracted with DCM. The aqueous layer was cooled further on ice, acidified to pH=1 and the solid residue was filtered off and dried, yielding 33 g of intermediate (21).

c) Preparation of

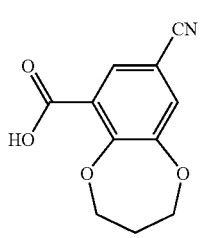
intermediate (22)

A mixture of intermediate (21) (0.33 mol) and copper(I) cyanide (2.7 mol) in DMA (800 ml) was stirred at 140° C. for 20 hours, then the reaction mixture was cooled and $FeCl_3.6H_2O$ (130 g), HCl (33 ml) and water (200 ml) were added. The mixture was stirred at 60° C. for 20 hours, cooled and poured out into water. Ethyl acetate was added and the layers were filtered to remove insoluble salts. The organic layer was separated, washed with water, dried, filtered and the solvent was evaporated. The residue was taken up in water and a 5% NaOH solution. was added, then the mixture was extracted with DIPE, acidified with HCl and extracted with ethyl acetate. The organic layer was separated, dried and the solvent was evaporated. The residue was purified by short column chromatography (eluent: $CH_2Cl_2/CH_3OH$ 95/5+2 ml acetic acid), yielding 7 g of intermediate (22).

Example A.9 a) Preparation of

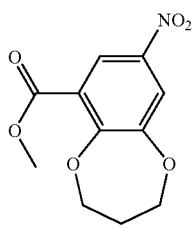

intermediate (23)

A mixture of 5-nitro-2,3-dihydroxybenzoic acid methyl-ester (0.3 mol), potassium carbonate (0.66 mol), 1,3-dibromopropane (0.42 mol) and tetra-n-butylammonium bromide (4.5 g) in 2-propanone (900 ml) and DMA (600 ml) was stirred and refluxed for 30 hours. The reaction mixture was stirred for two days at room temperature and then filtered. The solvent was evaporated and the residue was partitioned between water and DCM. The separated organic layer was dried, filtered and concentrated. The residue was suspended in DIPE, filtered, dried and purified by column chromatography over silica gel (eluent: $CH_2Cl_2/CH_3OH$ 98/2), yielding 33.5 g of intermediate (23).

b) Preparation of

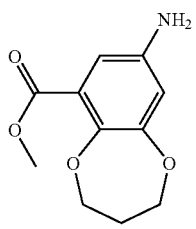

intermediate (24)

A mixture of intermediate (23) (0.11 mol) in THF (250 ml) was hydrogenated with palladium-on-carbon 10% (3 g) as a catalyst in the presence of a thiophene-solution (1 ml). After uptake of hydrogen (3 equivalents), the catalyst was filtered off over dicalite and the filtrate was concentrated, yielding 24.7 g of intermediate (24).

c) Preparation of

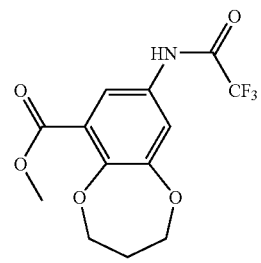

intermediate (25)

Intermediate (24) (0.11 mol) was dissolved in trichloromethane (500 ml) and the mixture was cooled on an ice-bath to a temperature below 10° C. Trifluoroacetic acid anhydride (0.14 mol) was added dropwise at the same temperature and then the reaction mixture was stirred for 1 hour at room temperature. The residue was crystallized from DIPE at room temperature overnight, yielding 5.8 g of intermediate (25).

d) Preparation of

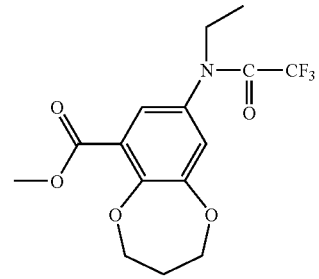

intermediate (26)

NaH 60% (0.171 mol) was added portionwise at room temperature to a mixture of intermediate (25) (0.131 mol) in DMF (450 ml) under a nitrogen flow. The mixture was stirred at room temperature for 1 hour. Iodoethane (0.171 mol) was added dropwise. The mixture was stirred at a temperature between 50 and 60° C. for 2 days, then cooled to room temperature, poured out into ice water and extracted with ethyl acetate. The organic layer was washed with water, dried, filtered and the solvent was evaporated. The residue was purified by column chromatography over silica gel (eluent: toluene/ethyl acetate 90/10), yielding 26.5 g of intermediate (26).

e) Preparation of

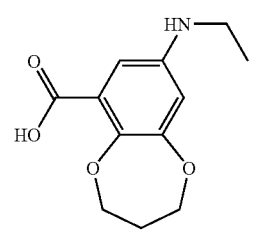

intermediate (27)

Lithiumhydroxide monohydrate (0.264 mol) was added portionwise at room temperature to a mixture of intermediate (26) (0.063 mol) in water (150 ml). The mixture was stirred at room temperature for 18 hours. Water (150 ml) was removed by evaporation. The mixture was acidified with HCl 3N till a pH=4 was obtained, then extracted with ethyl acetate. The organic layer was separated, dried, filtered, and the solvent was evaporated, yielding 14 g of intermediate (27).

Example A.10

Preparation of

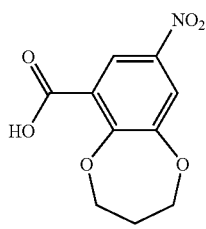

intermediate (28)

A mixture of intermediate (23) (0.12 mol) in NaOH 1N (200 ml) was stirred and refluxed for 4 hours. The reaction mixture stood overnight at room temperature, then cooled on an ice-bath and a HCl-solution 1N (200 ml) was added. The mixture was allowed to warm to room temperature and the formed precipitate was filtered, yielding 26.7 g of intermediate (28).

Example A.11 a) Preparation of

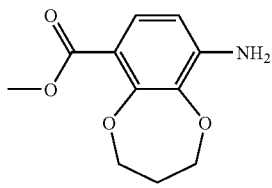

intermediate (29)

Sulfuric acid 97% (80 ml) was added carefully to a mixture of methyl 9-(acetylamino)-3,4-dihydro-2H-1,5-benzodioxepin-6-carboxylate (0.51 mol) in methanol (1000 ml). The mixture was stirred at 60° C. for 1 hour and then cooled. The solvent was evaporated. The residue was taken up in DCM. The mixture was washed with a KHCO$_3$ solution. The organic layer was separated, dried, filtered and the solvent was evaporated. The residue was suspended in DIPE and a small amount of ACN. The precipitate was filtered off, washed and dried, yielding 105 g of intermediate (29).

b) Preparation of

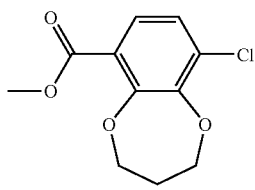

intermediate (30)

A mixture of intermediate (29) (0.24 mol) in water (240 ml) was stirred at 0° C. HCl (120 ml) was added dropwise at 0° C. The mixture was stirred for 15 minutes. A mixture of sodium nitrite (0.24 mol) in water (120 ml) was added dropwise at 0° C. The mixture was stirred at 0° C. for 30 minutes to give mixture A. A mixture of copper chloride (0.24 mol) in HCl (120 ml) was stirred at room temperature. Mixture A was added dropwise. The reaction mixture was stirred at room temperature for 1 hour. The precipitate was filtered off and washed and dried, yielding 55.8 g of intermediate (30).

c) Preparation of

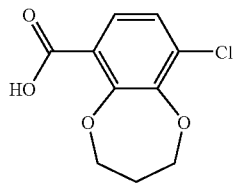

intermediate (31)

A mixture of intermediate (30) (0.22 mol) and KOH (2.2 mol) in water (1000 ml) was stirred and refluxed for 30 minutes and then cooled. The mixture was acidified with a concentrated HCl solution. The precipitate was filtered off, washed and dried, yielding 48 g of intermediate (31).

d) Preparation of

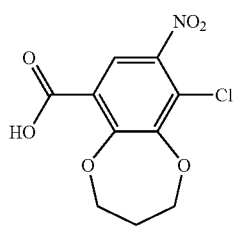

intermediate (32)

A mixture of intermediate (31) (0.01 mol) in sulfuric acid (20 ml) was cooled to −30° C., then a mixture of nitric acid (0.01 mol) in sulfuric acid (20 ml) was added dropwise at −30° C. and the reaction mixture was stirred for 5 minutes. The mixture was poured out into ice-water, the resulting precipitate was filtered off and washed with water, yielding intermediate (32).

Example A.12 a) Preparation of

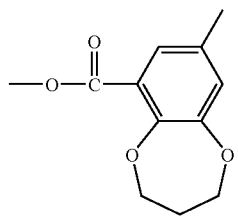

intermediate (33)

A mixture of methyl 2,3-dihydroxy-5-methylbenzoate (0.27 mol) and K$_2$CO$_3$ (0.6 mol) in 1,2-dibromoethane (0.4 mol) and acetone (1000 ml) was stirred and refluxed for 24 hours. The reaction mixture was cooled, filtered and the solvent was evaporated. The residue was taken up in DCM, washed with water and an aqueous 2N NaOH solution. The organic layer was dried, filtered and the solvent was evaporated, yielding 30.5 g of intermediate (33).

b) Preparation of

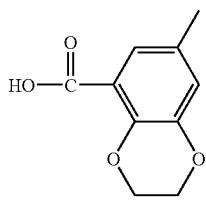
intermediate (34)

A solution of intermediate (33) (0.146 mol) in NaOH (2N) (400 ml) and THF (400 ml) was stirred and refluxed for 18 hours. The reaction mixture was cooled and THF was removed by evaporation. The residue was acidified with concentrated HCl. The resulting solid was filtered off, washed and dried, yielding 26.5 g of intermediate (34).

Example A.13 a) Preparation of

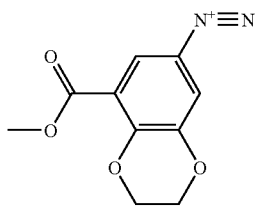
intermediate (35)

Intermediate (43) (0.086 mol) was added portionwise to a solution of concentrated HCl (18 ml) in water (18 ml). The mixture was cooled to 5° C. A solution of sodium nitrite (0.086 mol) in water (18 ml) was added dropwise. The mixture was stirred at 10° C. for 1 hour. The precipitate was filtered. The filtrate was cooled, then added to a solution of NaBF$_4$ (0.146 mol) in water (36 ml). The mixture was stirred for 30 minutes. The precipitate was filtered, washed with water, then with diethyl ether an dried in a vacuo at 40° C. for 12 hours, yielding 20 g of intermediate (35).

b) Preparation of

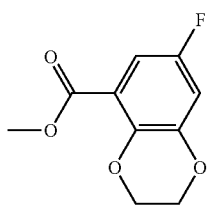
intermediate (36)

A mixture of intermediate (35) (0.0649 mol) and sodium fluoride (0.259 mol) in toluene (250 ml) was stirred and refluxed for two days. The solvent was evaporated till dryness. The residue was purified by column chromatography over silica gel (eluent: cyclohexane/EtOAc 80/20). The pure fractions were collected and the solvent was evaporated, yielding 7.6 g of intermediate (36).

c) Preparation of

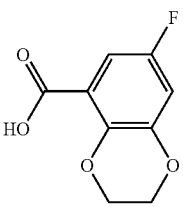
intermediate (37)

A mixture of intermediate (36) (0.0358 mol) and lithium hydroxide (0.0716 mol) in THF (70 ml) and water (70 ml) was stirred at room temperature overnight. The solvent was evaporated. The residue was acidified with HCl 6N. The precipitate was filtered, washed with water, then dissolved in CH$_2$Cl$_2$/CH$_3$OH. The organic layer was separated, dried, filtered, and the solvent was evaporated, yielding 6.22 g of intermediate (37).

Example A.14 a) Preparation of

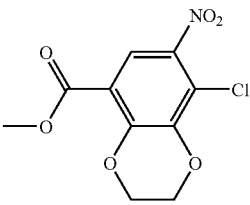
intermediate (38)

Methyl 8-cloro-2,3-dihydro-1,4-benzodioxin-5-carboxylic acid ester (0.44 mol) was dissolved in sulfuric acid (850 ml). This solution was cooled to below 0° C. Nitric acid (fuming, 0.44 mol) in sulfuric acid (200 ml) was added dropwise in 2 hours. The reaction mixture was stirred for 45 minutes at −10° C., then poured out into ice-water. Extraction with DCM yielded intermediate (38).

b) Preparation of

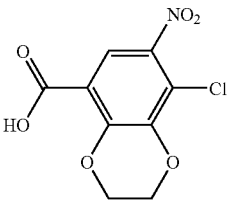
intermediate (39)

A mixture of intermediate (38) (0.20 mol) in THF (1000 ml) and NaOH (2N, 1000 ml) was stirred at room temperature for 5 hours. THF (700 ml) was removed by evaporation at 35° C. The aqueous layer was extracted with ethyl acetate (2×750 ml). The separated aqueous layer was cooled on an ice bath and acidified with concentrated HCl. The precipitate was filtered off, washed with water and dried, yielding 52 g of intermediate (39).

Example A.15 a) Preparation of

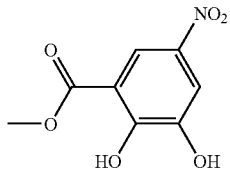

intermediate (40)

A mixture of 5-amino-2,3-dihydroxy benzoic acid (0.62 mol) in sulfuric acid (110 ml) and methanol (1100 ml) was stirred and refluxed for 24 hours. The reaction mixture stood overnight at room temperature. Then the mixture was concentrated and the residue was partitioned between DCM and water. The separated aqueous layer was washed with DCM and the separated organic layers were collected, dried, filtered and concentrated. The product was dried, yielding 120 g of intermediate (40).

b) Preparation of

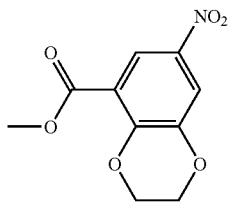

intermediate (41)

A mixture of intermediate (40) (0.35 mol), K$_2$CO$_3$ (0.77 mol) and tetrabutylammonium bromide (5 g) in 1,2-dibromoethane (42 ml), DMA (680 ml) and 2-propanone (1000 ml) was stirred and refluxed (70° C.) for 20 hours. Extra DMA (250 ml), tetrabutyl-ammonium bromide (5 g) and 1-bromo-2-chloroethane (29 ml) was added. The reaction mixture was stirred and refluxed for 44 hours. Then the reaction mixture was allowed to cool to room temperature over weekend. The suspension was filtered and the filtrate was concentrated. The concentrate was partitioned between water and toluene. The separated aqueous layer was washed several times with DCM. The separated organic layers were combined, dried, filtered and concentrated. The residue was crystallized from DIPE and ACN, yielding 26 g of intermediate (41) (mp. 140° C.).

c) Preparation of

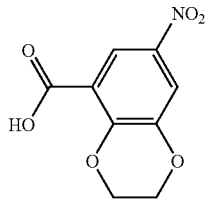

intermediate (42)

A mixture of intermediate (41) (0.063 mol) in NaOH 1N (100 ml) was stirred and refluxed for 4 hours. The reaction mixture was cooled on an ice-bath. A HCl-solution 1N (100 ml) was added to the formed precipitate. This reaction mixture was allowed to warm to room temperature and the formed precipitate was filtered and dried, yielding 14.5 g of intermediate (42) (mp. 234° C.).

Example A.16 a) Preparation of

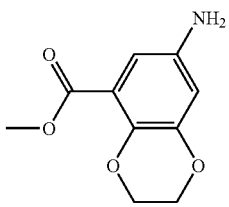

intermediate (43)

A mixture of intermediate (41) (0.089 mol) in methanol (500 ml) was hydrogenated at 50° C. with palladium-on-carbon (10%; 3 g) as a catalyst in the presence of thiophene solution (1 ml). After uptake of hydrogen (3 equivalents), the catalyst was filtered off over dicalite and the filtrate was evaporated, yielding 20.9 g of intermediate (43).

b) Preparation of

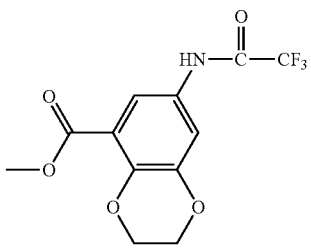

intermediate (43a)

To a mixture of intermediate (43) (0.1 mol) in trichloromethane (130 ml), trifluoro-acetic acid anhydride (0.11 mol) was added. The reaction mixture was stirred for 1 hour and the mixture was concentrated. The residue was purified over silica gel on a glass filter (eluent: CH$_2$Cl$_2$/MeOH 90/10). The product fractions were collected and the filtrate was concentrated. The residue was purified by column chromatography over silica gel (eluent: CH$_2$Cl$_2$/MeOH 98/2). The pure fractions were collected and the solvent was evaporated, yield 11.0 g of intermediate (43a).

c) Preparation of

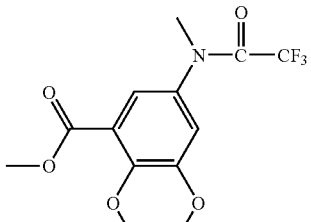

intermediate (44)

Intermediate (43a) (0.036 mol) in DMF (100 ml) was stirred at room temperature under nitrogen flow. Sodium hydride 60% in paraffine (0.0432 mol) was added portionwise under nitrogen flow. This reaction mixture was warmed to 50° C. Then iodomethane (0.0432 mol) was added dropwise at 50° C. under nitrogen flow. This reaction mixture was stirred at 50° C. overnight, then the mixture was allowed to cool to room temperature and was poured out in water (680 ml), then extracted with toluene. The separated organic layer was dried, filtered and concentrated, yielding 10.8 g of intermediate (44).

d) Preparation of

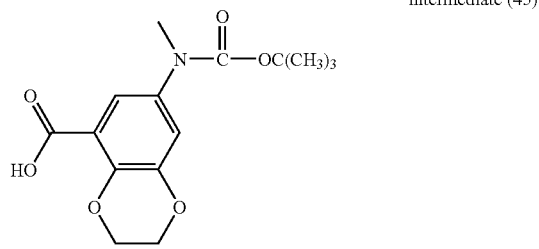

intermediate (45)

A mixture of intermediate (44) (0.0338 mol) in NaOH 1N (0.07 mol) and water (60 ml) was stirred and refluxed for 1 hour. The reaction mixture was allowed to cool to room temperature, then tert-butyl dicarbonate (0.041 mol) was added and the reaction mixture was stirred overnight at room temperature. Then HCl 1N (0.07 mol) was added and the residue was extracted with DCM. The separated organic layer was dried, filtered and concentrated, yielding 10.0 g of intermediate (45).

Example A.17

Preparation of

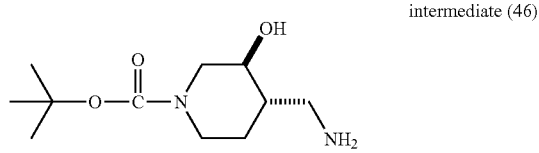

intermediate (46)

A mixture of 1,1-dimethylethyl(trans)-3-hydroxy-4-[[(phenylmethyl)amino]methyl]-1-piperidinecarboxylate [described in WO-00/37461 as intermediate (1-d)] (0.023 mol) in methanol (100 ml) was hydrogenated with palladium-on-carbon (10%, 1 g) as a catalyst. After uptake of hydrogen (1 equivalent), the catalyst was filtered off and the filtrate was evaporated. The residue was solidified in DIPE+ACN, filtered off and dried, yielding 4 g of 1,1-dimethylethyl(trans)-4-(aminomethyl)-3-hydroxy-1-piperidinecarboxylate (intermediate 46, mp. 178° C.).

Example A.18 a) Preparation of

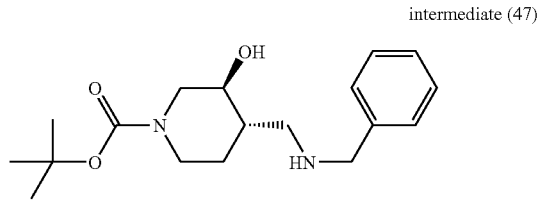

intermediate (47)

1,1-Dimethylethyl(trans)-3-hydroxy-4-[[(phenylmethyl)amino]methyl]-1-piperidinecarboxylate [described in WO-00/37461 as intermediate (1-d)] (2.73 mol) was separated and purified by chiral column chromatography over Chiralcel AD (eluent: hexane/ethanol 80/20). The desired fractions were collected and the solvent was evaporated. Toluene was added and azeotroped on the rotary evaporator, yielding 377 g of 1,1-dimethylethyl (3S-trans)-3-hydroxy-4-[[(phenylmethyl)amino]methyl]-1-piperidinecarboxylate (intermediate 47).

b) Preparation of

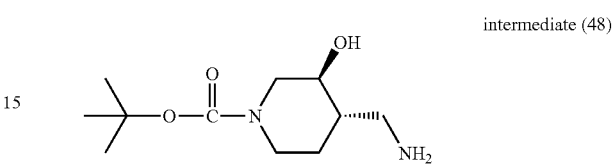

intermediate (48)

A mixture of intermediate (47) (0.028 mol) in methanol (100 ml) was hydrogenated with palladium-on-carbon (10%, 2 g) as a catalyst. After uptake of hydrogen (1 equivalent) the catalyst was filtered off and the filtrate was evaporated, yielding 4.7 g of 1,1-dimethylethyl (3S-trans)-4-(aminomethyl)-3-hydroxy-1-piperidinecarboxylate (intermediate (48); $[\alpha]_D^{20}$=+4.37° (c=24.03 mg/5 ml in $CH_3OH$)).

Example A.19 a) Preparation of

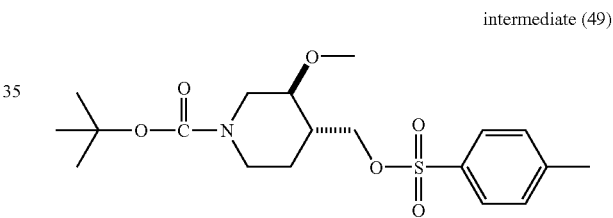

intermediate (49)

Reaction under nitrogen atmosphere. Sodiumhydride (0.3 mol) was added to a solution of 1,1-dimethylethyl trans-3-hydroxy-4-[[[(4-methylphenyl)sulfonyl]oxy]methyl]-1-piperidinecarboxylate [described in WO-00/37461 as intermediate (1-c)] (0.27 mol) in THF (1300 ml). The mixture was stirred for 30 minutes. Methyliodide (0.54 mol) was added and the resulting reaction mixture was stirred for 90 minutes. A small amount of water was added. The solvent was evaporated and the residue was partitioned between water and DCM. The organic layer was separated, dried, filtered and the solvent was evaporated, yielding 1,1-dimethylethyl trans-4-[[[(4-methylphenyl)sulfonyl]oxy]-methyl]-3-methoxy-1-piperidinecarboxylate (intermediate 49).

b) Preparation of

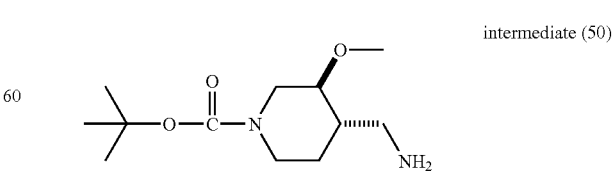

intermediate (50)

A mixture of intermediate (49) (0.065 mol) in THF (250 ml) was treated with liquid $NH_3$ in an autoclave at 125° C. during 16 hours. The reaction mixture was filtered and the filtrate was evaporated. The residue was partitioned between a 5% aqueous NaOH solution and DCM. The organic layer was separated, dried, filtered and the solvent was evaporated, yielding 16 g of 1,1-dimethylethyl(trans)-4-(aminomethyl)-3-methoxy-1-piperidinecarboxylate (intermediate (50)).

Example A.20 a) Preparation of

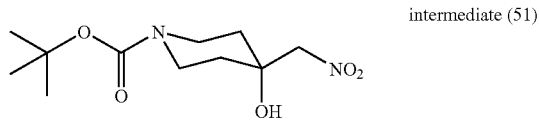

intermediate (51)

A mixture of tert-butyl 4-oxo-1-piperidinecarboxylate (0.1 mol) and nitro-methane (0.1 mol) in methanol (200 ml) was stirred at 10° C. Sodium methanolate (0.11 mol) was added dropwise at 10° C. The reaction mixture was stirred for 20 hours at room temperature. The solvent was evaporated. The residue was taken up into water, then neutralized with acetic acid, then extracted twice with DCM. The separated organic layer was washed with water, dried, filtered and the solvent evaporated. The residue was suspended in DIPE, filtered off, washed and dried, yielding 17.2 g of intermediate (51) (mp. 160° C.).

b) Preparation of

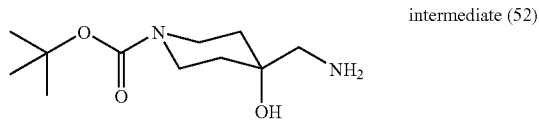

intermediate (52)

A mixture of intermediate (51) (0.058 mol) and acetic acid (12 ml) in methanol (250 ml) was hydrogenated at 14° C. with palladium-on-carbon (10%, 1 g) as a catalyst. After uptake of hydrogen (3 equivalents), the catalyst was filtered off and the filtrate was evaporated. The residue was taken up into ice/water, then alkalized with potassium hydroxide and salted out with $K_2CO_3$. This mixture was extracted twice with DCM. The separated organic layer was dried, filtered and the solvent evaporated. The residue was suspended in DIPE, filtered off, washed and dried, yielding 7.5 g of intermediate (52).

c) Preparation of intermediate (53)

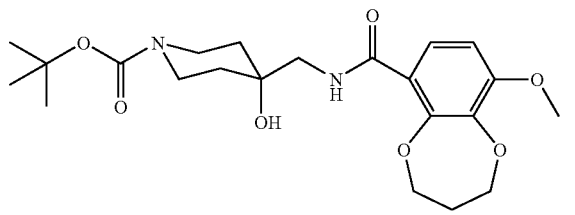

Triethylamine (0.0373 mol, 5.2 ml) then ethyl chloroformate (0.0373 mol) were added dropwise at a temperature between 0° C. and 5° C. to a mixture of intermediate (8) (0.0373 mol) in DCM (100 ml) under nitrogen flow. The mixture was stirred at this temperature for 45 minutes (first mixture). Triethylamine (0.0373 mol, 5.2 ml) was added at room temperature to a mixture of intermediate (52) (0.0373 mol) in DCM (100 ml). The mixture was stirred at room temperature for 45 minutes, then added dropwise at a temperature between 0° C. and 5° C. to the first mixture. The reaction mixture was stirred at this temperature for 1 hour, then brought to room temperature, stirred for 1 hour and poured out into ice water. DCM was added. The mixture was extracted with DCM. The organic layer was separated, dried, filtered, and the solvent was evaporated. The residue was purified by column chromatography over silica gel (eluent: $CH_2Cl_2/CH_3OH/NH_4OH$ 97/3/0.1). The pure fractions were collected and the solvent was evaporated, yielding 12 g of intermediate (53).

d) Preparation of intermediate (54)

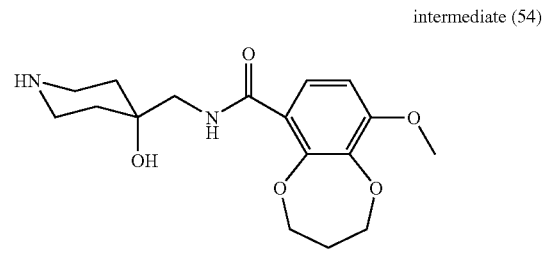

A mixture of intermediate (53) (0.0275 mol) in HCl/2-propanol (12 ml) and 2-propanol (120 ml) was stirred at 50° C. overnight, then brought to room temperature. The precipitate was filtered, washed with diethyl ether and dried, yielding 8.2 g of intermediate (54).

In an analogous way, intermediate (55) was prepared.

intermediate (55)

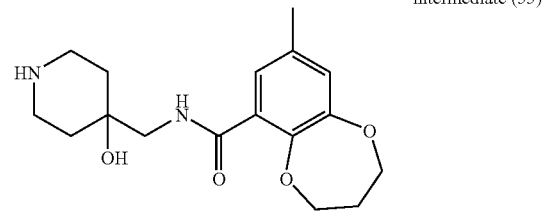

Example A.21 a) Preparation of intermediate (56)

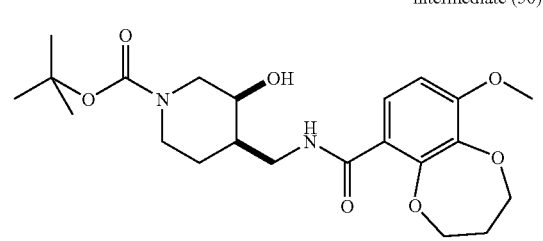

Triethylamine (0.03 mol) was added to a mixture of intermediate (8) (0.03 mol) in trichloromethane. Then, ethyl chloroformate (0.03 mol) was added at a temperature below 10° C. The mixture was stirred for 45 minutes, giving the mixture (I). A mixture of 1,1-dimethylethyl cis-3-hydroxy-4-[[[(4- methylphenyl)sulfonyl]oxy]methyl]-1-piperidinecarboxylate [described in WO-00/37461 as intermediate (1-f)] (0.03 mol) in trichloromethane was poured out into mixture (I) and the reaction mixture was stirred for 30 minutes, washed with a 5% aqueous NaOH solution, with water, dried, filtered and the solvent was evaporated, yielding 14 g of intermediate (56).

b) Preparation of intermediate (57)

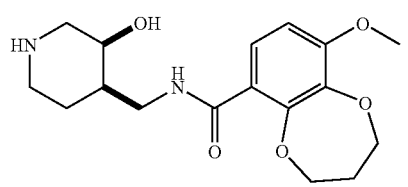

A mixture of intermediate (56) (0.03 mol), HCl/2-propanol (30 ml) and 2-propanol (300 ml) was stirred and refluxed for 30 minutes. The mixture was cooled and the solvent was evaporated. The residue was acidified with a 5% HCl solution and the mixture was extracted with DCM. The organic layer was separated. The aqueous layer was alkalised with a 5% NaOH solution and was extracted with DCM. The organic layer was separated, dried, filtered and the solvent was evaporated, yielding 8 g of intermediate (57).

In an analogous way, intermediates (58) and (59) were prepared.

intermediate (58)

intermediate (59)

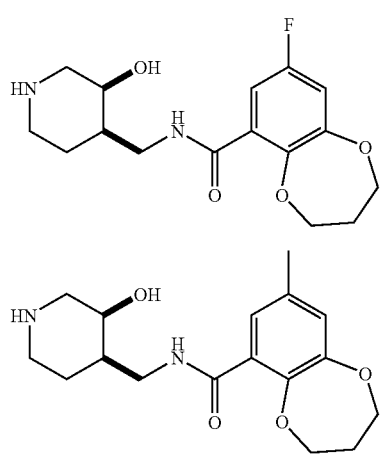

Example A.22 a) Preparation of (intermediate 60)

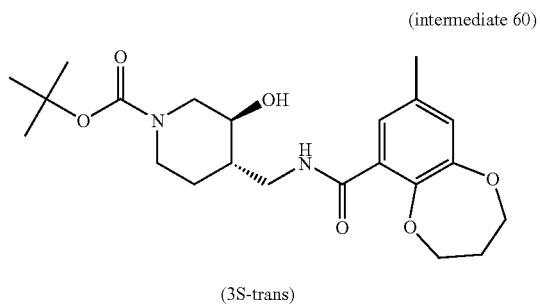

(3S-trans)

A mixture of intermediate (2) (0.336 mol) and triethylamine (0.4 mol) in DCM (1000 ml) was stirred at 5° C., then ethyl chloroformate (0.35 mol) was added dropwise and the reaction mixture was stirred for 30 minutes. To this mixture, a solution of intermediate (48) (83 g) in DCM (1000 ml) was added at 5° C., then the reaction mixture was allowed to reach room temperature and was washed with water. The organic layer was separated, dried, filtered and the solvent was evaporated, yielding 150 g of intermediate (60).

b) Preparation of (intermediate 61)

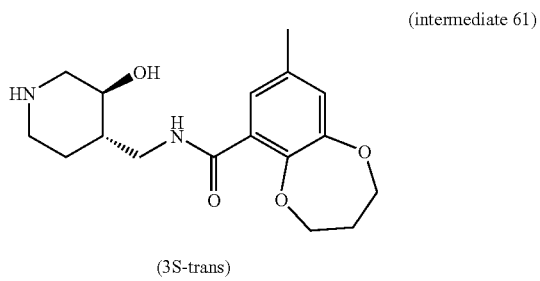

(3S-trans)

A mixture of intermediate (60) (0.336 mol) in 2-propanol saturated with HCl (160 ml) and 2-propanol (1400 ml) was stirred and refluxed for 1 hour. The solvent was evaporated and the residue was taken up in a mixture of DCM and a small amount of methanol. The mixture was washed with an aqueous ammonia solution and the organic layer was separated, dried, filtered. The solvent was evaporated, yielding 71 g of intermediate (61).

TABLE I-1 intermediates (62) to (88) were prepared according to the same procedure of Example A.20

| Intm. | Structure | Physical data |
|---|---|---|
| 62 | (structure with OH, piperidine-HN, HN-C(=O), NH₂, Cl, dioxine ring) | trans; •HCl (1:2) |

TABLE I-1-continued intermediates (62) to (88) were prepared according to the same procedure of Example A.20

| Intm. | Structure | Physical data |
|---|---|---|
| 63 | 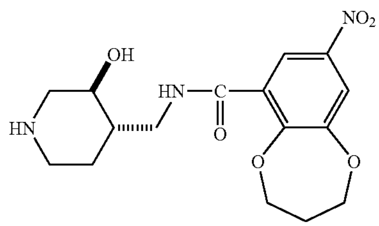 | trans; |
| 64 | 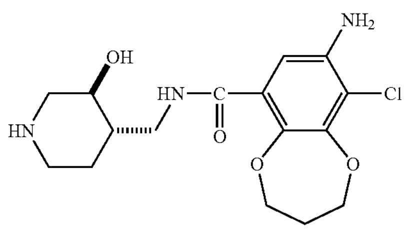 | trans; |
| 65 | 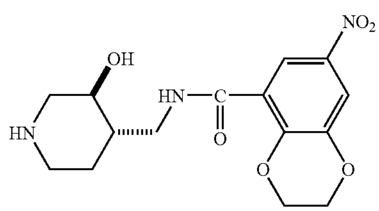 | trans; •HCl (1:1) |
| 66 | 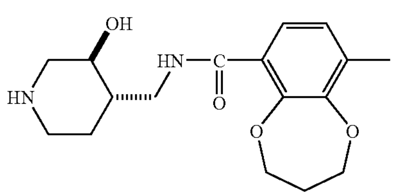 | trans; |
| 67 | 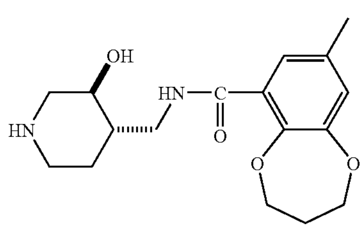 | trans; |
| 68 | 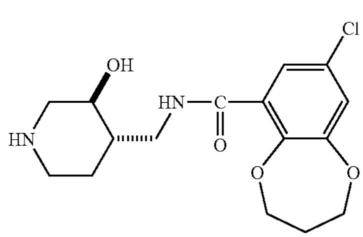 | trans; |

TABLE I-1-continued intermediates (62) to (88) were prepared according to the same procedure of Example A.20

| Intm. | Structure | Physical data |
|---|---|---|
| 69 | 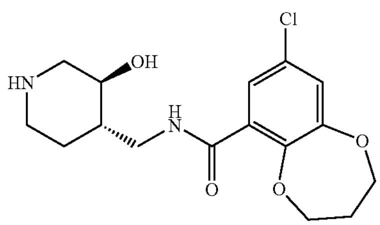 | 3S-trans; |
| 70 | 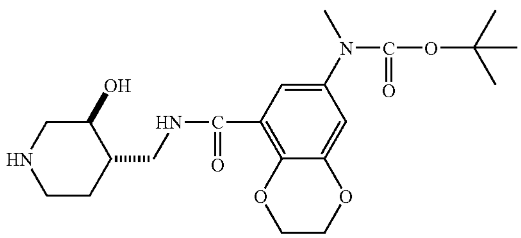 | trans; |
| 71 | 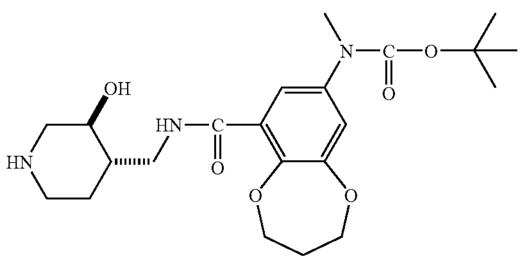 | trans; |
| 72 | 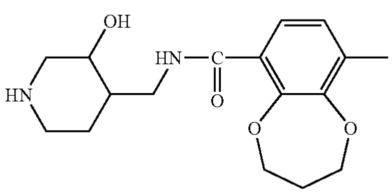 | |
| 73 | 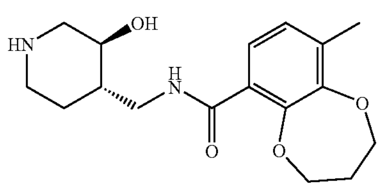 | 3S-trans; |
| 74 | 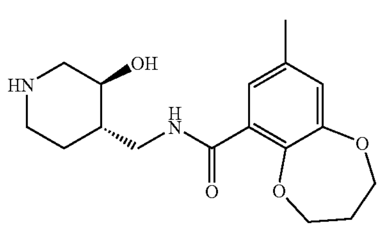 | 3S-trans; |

TABLE I-1-continued intermediates (62) to (88) were prepared according to the same procedure of Example A.20

| Intm. | Structure | Physical data |
|---|---|---|
| 75 | 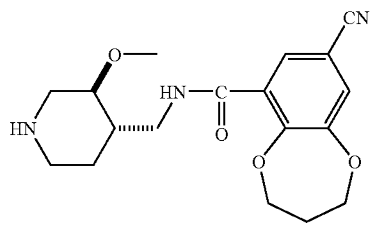 | trans; |
| 76 | 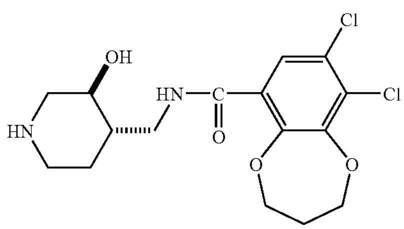 | trans; •HCl (1:1) |
| 78 | 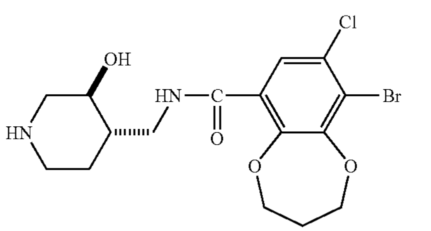 | trans; •HCl (1:1) |
| 79 | 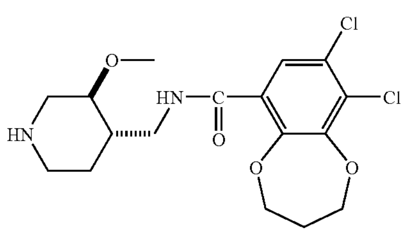 | trans; •HCl (1:1) |
| 80 | 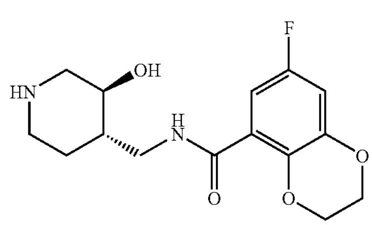 | 3S-trans; |
| 81 | 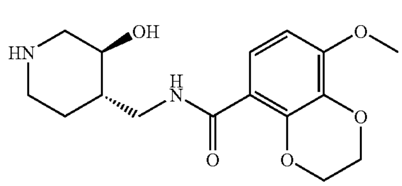 | 3S-trans; |

TABLE I-1-continued intermediates (62) to (88) were prepared according to the same procedure of Example A.20

| Intm. | Structure | Physical data |
|---|---|---|
| 82 | 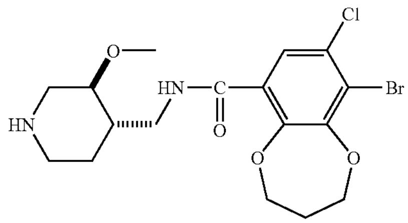 | trans; |
| 83 | 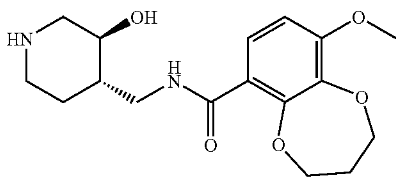 | 3S-trans; |
| 84 | 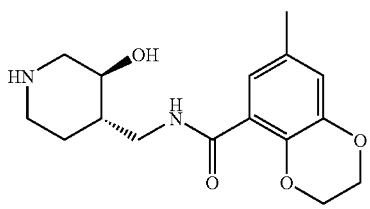 | 3S-trans; |
| 85 | 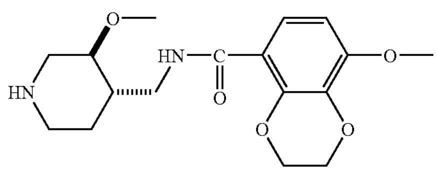 | trans; |
| 86 | 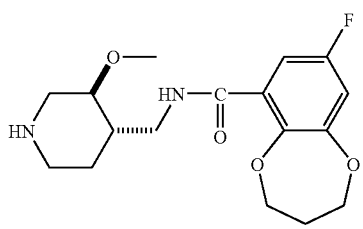 | trans; |
| 87 | 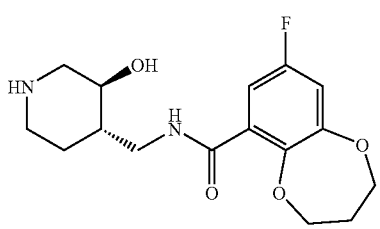 | 3S-trans; |
| 88 | 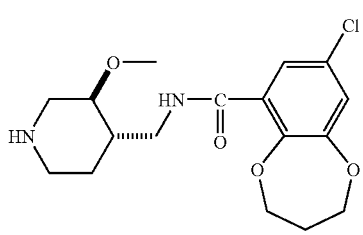 | trans; |

B. Preparation of the Final Compounds

Example B.1

A mixture of intermediate (62) (0.008 mol), 3-chloro-1-propanesulfonamide (0.012 mol) and $Na_2CO_3$ (0.03 mol) in 2-butanol (100 ml) was stirred and refluxed for 40 hours. More 3-chloro-1-propanesulfonamide (0.02 mol) was added and the mixture was stirred and refluxed for 24 hours; then cooled. The sticky product precipitates. The solids were filtered off. The remaining sticky solid was dissolved in $CH_3OH/CH_2Cl_2$ and filtered. The filtrate was concentrated. Methanol was added to the concentrate. The residue was recrystallized from methanol. The solid was filtered off, washed with methanol and dried. The residue was triturated under $H_2O/CH_2Cl_2$, filtered, washed with water and dried, yielding 2.02 g of compound (1) (mp. 150° C.).

Example B.2 a) Preparation of

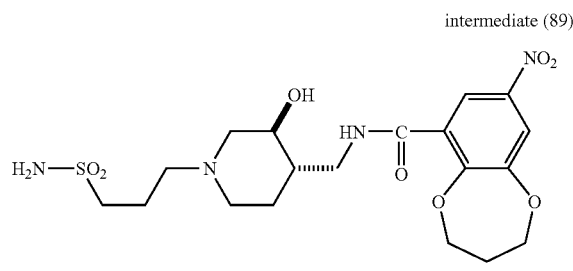

intermediate (89)

A mixture of intermediate (63) (0.01 mol), 3-chloro-1-propanesulfonamide (0.015 mol) and $Na_2CO_3$ (0.02 mol) in isobutanol (100 ml) was stirred and refluxed for 70 hours. The solvent was evaporated. The residue was taken up into DCM and methanol, then washed with water, dried, filtered and the solvent was evaporated. The residue was purified by column chromatography over silica gel (eluent: $CH_2Cl_2/(CH_3OH/NH_3)$ 90/10). The desired fractions were collected and the solvent was evaporated, yielding 0.9 g of intermediate (89).

b) A mixture of intermediate (89) (0.002 mol) in methanol (150 ml) was hydrogenated with palladium-on-carbon 10% (0.5 g) as a catalyst in the presence of thiophene solution (0.5 ml). After uptake of hydrogen (3 equivalents), the catalyst was filtered off and the filtrate was evaporated. The residue was purified by column chromatography over silica gel (eluent: $CH_2Cl_2/(CH_3OH/NH_3)$ 95/5). The product fractions were collected and the solvent was evaporated. The residue was dissolved in 2-propanol and a small amount of DIPE, and converted into the (E)-2-butenedioic acid salt (1:1), filtered off, washed and dried, yielding 0.72 g of compound (8) (mp. 186° C.).

Example B.3 a) Preparation of

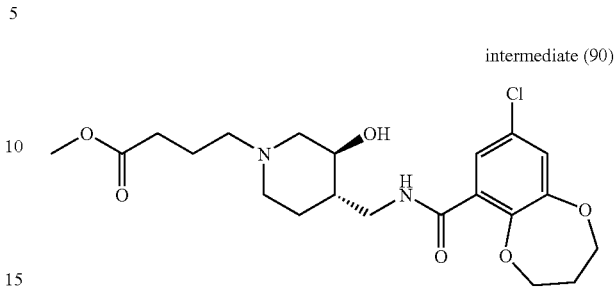

intermediate (90)

A mixture of intermediate (69) (0.05 mol), methyl 4-bromobutanoate (0.06 mol) and triethylamine (0.06 mol) in DMF (300 ml) was stirred for 20 hours at 70° C. The reaction mixture was cooled, taken up into water, then extracted with toluene. The separated organic layer was dried, filtered and the solvent evaporated. The residue was taken up into DCM, washed with water, dried, filtered and the solvent was evaporated. The residue was purified over silica gel on a glass filter (eluent: $CH_2Cl_2/(CH_3OH/NH_3)$ 95/5). The desired fractions were collected and the solvent was evaporated, yielding 17.1 g of intermediate (90).

b) Preparation of

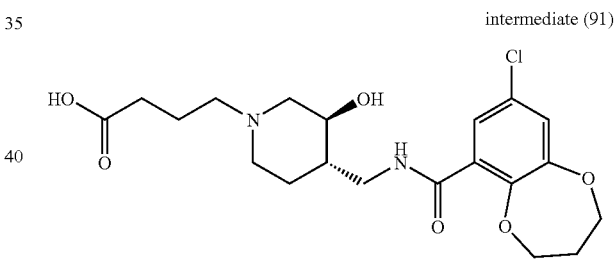

intermediate (91)

Intermediate (90) (0.036 mol) was dissolved in THF (35 ml). NaOH 1N (0.036 mol) was added dropwise over 2 hours at 18-20° C. (ice-bath). The mixture was stirred for 90 minutes at room temperature. 1 N NaOH (5 ml) was added and the mixture was stirred for one more hour. HCl 1N (0.036 mol) was added dropwise over one hour at 18-20° C. (ice-bath). The mixture was stirred for 2 hours at room temperature. The solvent was evaporated, yielding 17.5 g intermediate (91).

c) Triethylamine (0.01 mol) was added at 5° C. to a mixture of intermediate (91) (0.005 mol) in DCM (100 ml), then ethyl chloroformate (0.005 mol) was added dropwise at 5° C. and the reaction mixture was stirred at 5° C. for 1 hour. Methanesulfonamide (0.01 mol) was added at 5° C., the mixture was allowed to reach room temperature and was stirred at room temperature for 24 hours. The resulting precipitate was filtered off, washed and dried, yielding 1.05 g of compound (15) (mp. 110° C.; $[\alpha]_D^{20}=-14.96°$ (c=22.06 mg/5 ml in $CH_3OH$)).

Example B.4 a) Preparation of

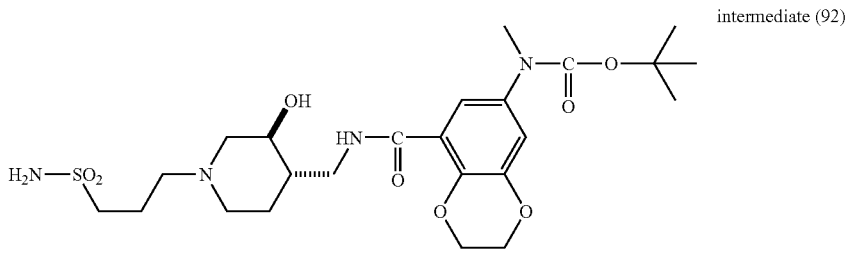
intermediate (92)

A mixture of intermediate (70) (0.01 mol), 3-chloro-1-propanesulfonamide (0.02 mol) and Na₂CO₃ (0.02 mol) in 2-methyl-1-propanol (100 ml) was stirred and refluxed for 48 hours, then filtered hot. The filtrate's solvent was evaporated. The residue was purified over silica gel on a glass filter (eluent: CH₂Cl₂/(CH₃OH/NH₃) 95/5), yielding 2 g of intermediate (92).

b) Intermediate (92) (0.0037 mol) in HCl/2-propanol (5 ml) and 2-propanol (60 ml) was stirred and refluxed for 1 hour, then cooled to room temperature. The precipitate was filtered off, washed and dried, yielding 1.08 g of compound (3) (mp. 130° C.).

Example B.5

A mixture of intermediate (69) (0.0117 mol) and ethenesulfonamide (0.0141 mol) in Copper (few) was stirred at 125° C. for 2 hours, then cooled to room temperature. CH₂Cl₂/CH₃OH (few)/H₂O were added. The mixture was basified with K₂CO₃. The organic layer was separated, dried, filtered, and the solvent was evaporated till dryness. The residue was purified by column chromatography over silica gel (eluent: CH₂Cl₂/CH₃OH/NH₄OH 90/10/1). The pure fractions were collected and the solvent was evaporated. The residue was crystallized from DIPE. The precipitate was filtered off and dried, yielding 2.506 g of compound (22) (mp. 162° C.; $[\alpha]_D^{20}=-8.81°$ (c=14.75 mg/2 ml in CH₃OH)).

Example B.6 a) Preparation of

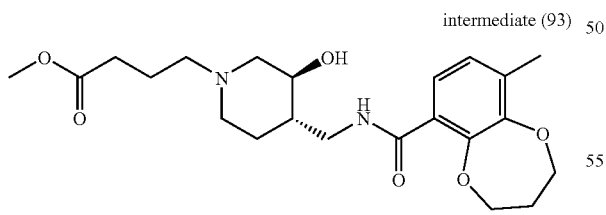
intermediate (93)

A mixture of intermediate (73) (0.036 mol), methyl 4-bromobutanoate (0.047 mol), triethylamine (0.09 mol) in DMF (200 ml) was stirred at 75° C. for 16 hours. The reaction mixture was cooled, poured out into water and extracted with toluene. The organic layer was dried, filtered off and the solvent was evaporated. The residue was purified over silica gel on a glass filter (eluent: CH₂Cl₂/(CH₃OH/NH₃) 97/3). The product fractions were collected and the solvent was evaporated, yielding 12.4 g) of intermediate (93).

b) Preparation of

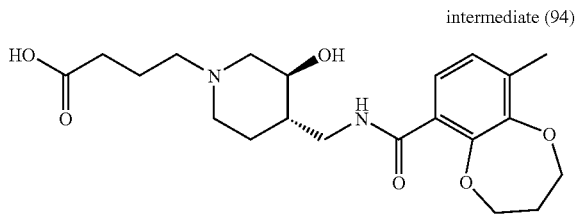
intermediate (94)

A mixture of intermediate (93) (0.0295 mol) in water (50 ml) was stirred at 95° C. over the weekend. The reaction mixture was cooled and the solvent was evaporated, yielding 8.5 g of intermediate (94).

c) Ethyl chloroformate (0.007 mol) was added dropwise to a mixture of intermediate (94) (0.007 mol), triethylamine (0.014 mol) in DCM (50 ml) at a temperature of 5° C. The reaction mixture was stirred at 5° C. for 1 hour. Methanesulfonyl chloride (0.014 mol) was added to the solution. The reaction mixture was stirred at room temperature for 24 hours and washed with water. The organic layer was dried, filtered off and the solvent was evaporated. The residue was purified by flash column chromatography over Biotage (eluent: CH₂Cl₂/CH₃OH 99/1, 97/3, 96/4, 94/6). The product fractions were collected and the solvent was evaporated. The residue was crystallised from DIPE, yielding 0.7 g (21%) of compound (27) (mp. 142° C.; $[\alpha]_D^{20}=-14.24°$ (c=9.83 mg/5 ml in CH₃OH)).

Example B.7

Sodiumhydride 60% in oil (0.0033 mol) was added at room temperature to a mixture of compound (36) (0.0027 mol) in DMF (15 ml). The mixture was stirred at room temperature for 1 hours. Methanesulfonyl chloride (0.0027 mol) was added. The mixture was stirred for 48 hours, poured out into ice water, saturated with K₂CO₃ and extracted with ethyl acetate. The organic layer was separated, dried, filtered, and the solvent was evaporated. The residue was purified by column chromatography over silica gel (eluent: CH₂Cl₂/CH₃OH/NH₄OH 80/20/2). The pure fractions were collected and the solvent was evaporated. The residue was dissolved in DCM, washed with H₂O/K₂CO₃, saturated with K₂CO₃. The organic layer was separated, dried, filtered, and the solvent was evaporated, yielding 0.21 g of compound (37).

Tables F-1 to F-4 list the compounds that were prepared according to one of the above Examples.

TABLE F-1

| Co. No. | Ex. No. | —L | $R^3$ | $R^4$ | $R^5$ | Physical data |
|---|---|---|---|---|---|---|
| 1 | B.1 | $H_2N-SO_2-(CH_2)_3-$ | Cl | $NH_2$ | H | trans; hydrate (1:1), mp. 150° C. |
| 2 | B.2 | $H_2N-SO_2-(CH_2)_3-$ | H | $NH_2$ | H | trans; hydrate (1:1), mp. 207° C. |
| 3 | B.4b | $H_2N-SO_2-(CH_2)_3-$ | H | $NHCH_3$ | H | trans; hydrochloride (2:3) hydrate (1:2) 2-propanolate (2:1), mp. 130° C. |
| 4 | B.1 | $H_2N-SO_2-(CH_2)_4-$ | $CH_3O$ | H | H | 3S-trans, mp. 190° C., $[\alpha]_D^{20} = -10.64°$ (c = 25.38 mg/5 ml in methanol) |
| 5 | B.1 | $H_2N-SO_2-(CH_2)_4-$ | H | $CH_3$ | H | 3S-trans, $[\alpha]_D^{20} = -11.82°$ (c = 10.66 mg/2 ml in methanol) |
| 6 | B.1 | $H_2N-SO_2-(CH_2)_4-$ | $CH_3O$ | H | $CH_3$ | trans; mp. >70° C. |
| 7 | B.1 | $H_2N-SO_2-(CH_2)_4-$ | H | F | H | 3S-trans; mp. 164° C. |

TABLE F-2

| Co. No. | Ex. No. | —L | $R^3$ | $R^4$ | Physical data |
|---|---|---|---|---|---|
| 8 | B.2b | $H_2N-SO_2-(CH_2)_3-$ | H | $NH_2$ | trans; E-2-butenedioate (1:1), mp. 186° C. |
| 9 | B.1 | $H_2N-SO_2-(CH_2)_3-$ | Cl | $NH_2$ | trans, mp. 158° C. |
| 10 | B.1 | $C_6H_5-NH-SO_2-(CH_2)_3-$ | $CH_3$ | H | trans, mp. 58° C. |
| 11 | B.1 | $(CH_3)_2CH-NH-SO_2-(CH_2)_3-$ | H | $CH_3$ | trans; ethanedioate (1:1), mp. 80° C. |
| 12 | B.1 | $C_6H_5-NH-SO_2-(CH_2)_3-$ | H | $CH_3$ | trans; hydrochloride (1:1), mp. 137° C. |
| 13 | B.1 | $(CH_3)_2CH-NH-SO_2-(CH_2)_3-$ | $CH_3$ | H | trans; hydrochloride (1:1), mp. 171° C. |
| 14 | B.1 | $(CH_3)_2CH-NH-SO_2-(CH_2)_3-$ | H | Cl | trans; ethanedioate (1:1), mp. 170° C. |
| 15 | B.3c | $CH_3-SO_2-NH-CO-(CH_2)_3-$ | H | Cl | 3S-trans, mp. 110° C., $[\alpha]_D^{20} = -14.96°$ (c = 22.06 mg/5 ml in methanol) |
| 16 | B.4 | $H_2N-SO_2-(CH_2)_3-$ | H | $CH_3NH$ | trans; E-2-butenedioate (2:1) hydrate (1:1) ethanolate (2:1), mp. 100° C. |
| 17 | B.1 | $C_6H_5-NH-SO_2-(CH_2)_3-$ | H | Cl | trans, mp. 90° C. |
| 18 | B.1 | $H_2N-SO_2-(CH_2)_3-$ | $CH_3$ | H | trans, mp. 126° C. |
| 19 | B.1 | $H_2N-SO_2-(CH_2)_3-$ | H | $CH_3$ | trans, mp. 82° C. |
| 20 | B.1 | $H_2N-SO_2-(CH_2)_4-$ | H | $CH_3$ | trans, mp. 170° C. |

TABLE F-2-continued

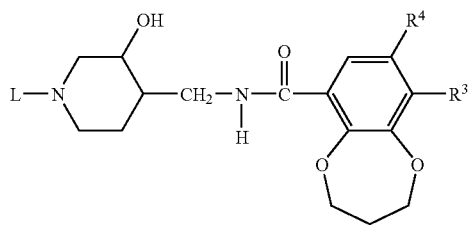

| Co. No. | Ex. No. | —L | R³ | R⁴ | Physical data |
|---|---|---|---|---|---|
| 21 | B.1 | H₂N—SO₂—(CH₂)₃— | H | Cl | trans, mp. 56° C. |
| 22 | B.5 | H₂N—SO₂—(CH₂)₂— | H | Cl | 3S-trans, mp. 162° C., $[\alpha]_D^{20}$ = −8.81° (c = 14.75 mg/2 ml in methanol) |
| 23 | B.5 | H₂N—SO₂—(CH₂)₂— | CH₃ | H | 3S-trans, mp. 200° C., $[\alpha]_D^{20}$ = −12.73° (c = 7.70 mg/2 ml in methanol) |
| 24 | B.1 | CH₃—NH—SO₂—(CH₂)₃— | H | CH₃ | trans, mp. 150° C. |
| 25 | B.5 | H₂N—SO₂—(CH₂)₂— | H | CH₃ | 3S-trans; mp. 166° C. |
| 26 | B.1 | H₂N—SO₂—(CH₂)₄— | H | Cl | 3S-trans, mp. 172° C., $[\alpha]_D^{20}$ = −7.89° (c = 10.64 mg/2 ml in methanol |
| 27 | B.6c | CH₃—SO₂—NH—CO—(CH₂)₃— | CH₃ | H | 3S-trans; hydrochloride (10:1), mp. 142° C.; $[\alpha]_D^{20}$ = −14.24° (c = 9.83 mg/5 ml in methanol) |
| 28 | B.3 | CH₃—SO₂—NH—CO—(CH₂)₃— | H | CH₃ | 3S-trans; hydrate (1:1), mp. 124° C.; $[\alpha]_D^{20}$ = −14.19° (c = 10.22 mg/5 ml in methanol) |
| 29 | B.1 | H₂N—SO₂—(CH₂)₄— | CH₃ | H | 3S-trans, mp. 190° C.; $[\alpha]_D^{20}$ = −10.50° (c = 10.10 mg/2 ml in methanol) |
| 30 | B.1 | H₂N—SO₂—(CH₂)₄— | Cl | Cl | trans, mp. 181° C. |
| 31 | B.1 | H₂N—SO₂—(CH₂)₄— | Br | Cl | trans, mp. 187° C. |
| 32 | B.1 | H₂N—SO₂—(CH₂)₄— | CH₃O | H | 3S-trans, $[\alpha]_D^{20}$ = −7.85° (c = 12.23 mg/2 ml in methanol) |
| 33 | B.1 | CH₃—NH—SO₂—(CH₂)₃— | H | Cl | trans; oxalate (1:1) |
| 34 | B.1 | CH₃—NH—SO₂—(CH₂)₃— | H | CH₃ | 3S-trans; oxalate (1:1), $[\alpha]_D^{20}$ = −10.69° (c = 7.86 mg/2 ml in methanol) |
| 35 | B.1 | H₂N—SO₂—(CH₂)₄— | H | F | 3S-trans, $[\alpha]_D^{20}$ = −10.39° (c = 10.01 mg/2 ml in methanol) |
| 36 | B.1 | H₂N—SO₂—(CH₂)₃— | H | CH₃ | 3S-trans |
| 37 | B.7 | CH₃—SO₂—NH—SO₂—(CH₂)₃— | H | CH₃ | 3S-trans; mp. 108° C. |
| 38 | B.1 | H₂N—SO₂—(CH₂)₄— | H | CH₃ | cis; mp. 122° C. |
| 39 | B.1 | H₂N—SO₂—(CH₂)₄— | H | F | cis |
| 40 | B.1 | H₂N—SO₂—(CH₂)₄— | CH₃O | H | cis |

TABLE F-3

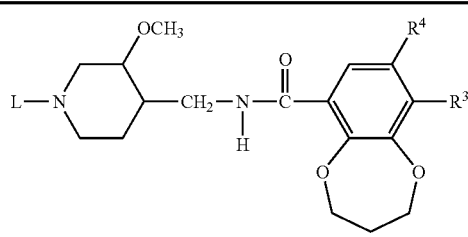

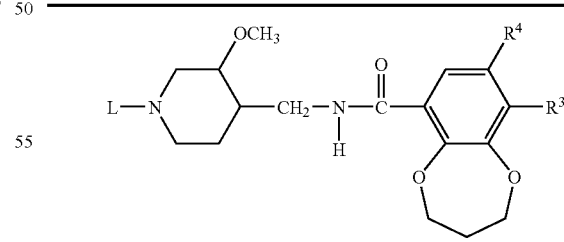

| Co. No. | Ex. No. | —L | R³ | R⁴ | Physical data |
|---|---|---|---|---|---|
| 41 | B.1 | H₂N—SO₂—(CH₂)₃— | H | CN | trans; oxalate (1:1), mp. 145° C. |
| 42 | B.1 | H₂N—SO₂—(CH₂)₄— | Cl | Cl | trans, mp. 156° C. |
| 43 | B.1 | H₂N—SO₂—(CH₂)₄— | Br | Cl | trans, mp. 120° C. |
| 44 | B.1 | H₂N—SO₂—(CH₂)₄— | H | F | trans; oxalate (1:1) |
| 45 | B.1 | H₂N—SO₂—(CH₂)₄— | H | Cl | trans |
| 46 | B.1 | H₂N—SO₂—(CH₂)₃— | H | F | trans; mp. 138° C. |

TABLE F-4

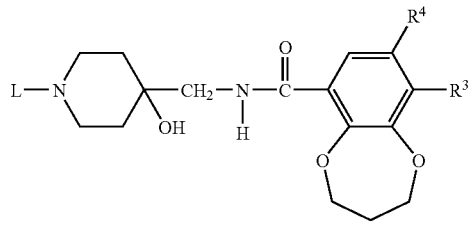

| Co. No. | Ex. No. | —L | R³ | R⁴ | Physical data |
|---|---|---|---|---|---|
| 47 | B.1 | H₂N—SO₂—(CH₂)₄— | CH₃O | H | — |
| 48 | B.1 | H₂N—SO₂—(CH₂)₄— | H | CH₃ | mp. 152° C. |

Pharmacological Examples

Example C.1

5HT$_4$ Antagonism h5-HT$_{4b}$-HEK 293 clone 9 cells were cultured in 150 mm Petri dishes and washed twice with cold PBS. The cells were then scraped from the plates and suspended in 50 mM Tris-HCl buffer, pH 7.4 and harvested by centrifugation at 23,500 rpm for 10 minutes. The pellet was resuspended in 5 mM Tris-HCl, pH 7.4 and homogenized with an Ultra Turrax homogenizer. The membranes were collected by centrifugation at 30,000 rpm for 20 min, resuspended in 50 mM Tris-HCl pH 7.4 and stored at −80° C. For the experiment, assay mixtures (0.5 ml) contained 50 μl of the tritiated ligand (5-HT$_4$ antagonist [³H]GR113808 0.1 nM) and 0.4 ml membrane preparation (15 μg protein/ml). 50 μl of 10% DMSO was added for total binding. 50 μl of 1 μM of (+)-trans-(1-butyl-3-hydroxy-4-piperidinyl)methyl 8-amino-7-chloro-2,3-dihydro-1,4-benzodioxin-5-carboxylate (a proprietary 5HT$_4$ agonist of Janssen Pharmaceutica) was added for determination of non-specific binding. The [³H]GR113808 assay buffer was 50 mM HEPES-NaOH, pH 7.4. The mixtures were incubated for 30 min at 25° C. The incubation was terminated by filtration over a Unifilter 96 GF/B presoaked in 0.1% polyethylenimine, followed by six washing steps with 50 mM HEPES-NaOH, pH 7.4. Ligand concentration binding isotherms (rectangular hyperbola) were calculated by nonlinear regression analysis and the pIC$_{50}$ data for all tested compounds are listed below in Table C.1.

TABLE C.1

5HT$_4$ antagonistic data

| Co. No. | pIC50 |
|---|---|
| 1 | 7.92 |
| 2 | 8.02 |
| 3 | 7.66 |
| 4 | 8.83 |
| 5 | 9.13 |
| 6 | 7.54 |
| 7 | 8.73 |
| 8 | 7.3 |
| 9 | 7.61 |
| 10 | 8.89 |
| 11 | 8.4 |
| 12 | 8.79 |
| 13 | 8.47 |
| 14 | 8.71 |
| 15 | 7.45 |
| 16 | 6.56 |
| 17 | 8.75 |
| 18 | 8.28 |
| 19 | 8.47 |
| 20 | 8.33 |
| 21 | 8.52 |
| 22 | 8.27 |
| 23 | 8.24 |
| 24 | 8.54 |
| 25 | 8.07 |
| 26 | 9.17 |
| 27 | 7.92 |
| 28 | 7.51 |
| 29 | 8.78 |
| 30 | 8.77 |
| 31 | 9.05 |
| 32 | 8.44 |
| 33 | 8.66 |
| 34 | 8.94 |
| 35 | 9.39 |
| 37 | 7.8 |
| 38 | 7.95 |
| 39 | 7.9 |
| 40 | 6.8 |
| 41 | 7.25 |
| 42 | 8.82 |
| 43 | 8.77 |
| 44 | 8.43 |
| 45 | 8.86 |
| 46 | 8.38 |
| 47 | 7 |
| 48 | 7.68 |

Example C.2

Metabolic Stability

Sub-cellular tissue preparations were made according to Gorrod et al. (Xenobiotica 5: 453-462, 1975) by centrifugal separation after mechanical homogenization of tissue. Liver tissue was rinsed in ice-cold 0.1 M Tris-HCl (pH 7.4) buffer to wash excess blood. Tissue was then blotted dry, weighed and chopped coarsely using surgical scissors. The tissue pieces were homogenized in 3 volumes of ice-cold 0.1 M phosphate buffer (pH 7.4).

Tissue homogenates were centrifuged at 9000×g for 20 minutes at 4° C. The resulting supernatant was stored at −80° C. and is designated 'S9'.

The S9 fraction can be further centrifuged at 100.000×g for 60 minutes (4° C.). The resulting supernatant was carefully aspirated, aliquoted and designated 'cytosol'. The pellet was re-suspended in 0.1 M phosphate buffer (pH 7.4) in a final volume of 1 ml per 0.5 g original tissue weight and designated 'microsomes'.

All sub-cellular fractions were aliquoted, immediately frozen in liquid nitrogen and stored at −80° C. until use.

For the samples to be tested, the incubation mixture contained PBS (0.1M), compound (5 μM), microsomes (1 mg/ml) and a NADPH-generating system (0.8 mM glucose-6-phosphate, 0.8 mM magnesium chloride and 0.8 Units of glucose-6-phosphate dehydrogenase). Control samples contained the same material but the microsomes were replaced by heat inactivated (10 minutes at 95 degrees Celsius) microsomes. Recovery of the compounds in the control samples was always 100%.

The mixtures were preincubated for 5 minutes at 37 degrees Celsius. The reaction was started at time point zero (t=0) by addition of 0.8 mM NADP and the samples were incubated for 60 minutes (t=60). The reaction was terminated by the addition of 2 volumes of DMSO. Then the samples were centrifuged for 10 minutes at 900×g and the supernatants were stored at room temperature for no longer as 24 hours before analysis. All incubations were performed in duplo. Analysis of the supernatants was performed with LC-MS analysis. Elution of the samples was performed on a Xterra MS C18 (50×4.6 mm, 5 μm, Waters, US). An Alliance 2790 (Supplier: Waters, US) HPLC system was used. Elution was with buffer A (25 mM ammoniumacetate (pH 5.2) in H₂O/acetonitrile (95/5)), solvent B being acetonitrile and solvent C methanol at a flow rate of 2.4 ml/min. The gradient employed was increasing the organic phase concentration from 0% over 50% B and 50% C in 5 min up to 100% B in 1 minute in a linear fashion and organic phase concentration was kept stationary for an additional 1.5 minutes. Total injection volume of the samples was 25 μl.

A Quatro triple quadrupole mass spectrometer fitted with and ESP source was used as detector. The source and the desolvation temperature were set at 120 and 350° C. respectively and nitrogen was used as nebuliser and drying gas. Data were acquired in positive scan mode (single ion reaction). Cone voltage was set at 10 V and the dwell time was 1 second.

Metabolic stability was expressed as % metabolism of the compound after 60 minutes (equation given as example) of incubation in the presence of active microsomes (E(act))

$$(\% \text{ metabolism} = 100\% - \left(\left(\frac{\text{Total Ion Current}(TIC) \text{ of } E(act) \text{ at } t = 60}{TIC \text{ of } E(act) \text{ at } t = 0}\right) \times 100\right).$$

TABLE C.2

| Co. No. | % metabolised |
|---|---|
| 4 | 11 |
| 5 | 13 |
| 6 | 9 |
| 7 | 3 |
| 15 | 36 |
| 18 | 7 |
| 19 | 14 |
| 20 | 2 |
| 21 | 21 |
| 22 | 28.5 |
| 23 | 8 |
| 24 | 53 |
| 25 | 8.5 |
| 26 | 13 |
| 27 | 5 |
| 28 | 6 |
| 29 | 17 |
| 30 | 12 |
| 31 | 18 |
| 32 | 0 |
| 35 | 15 |
| 38 | 3 |
| 39 | 2 |
| 40 | 0 |
| 44 | 27 |
| 47 | 0 |
| 48 | 6 |

The invention claimed is:

1. A compound of formula (I)

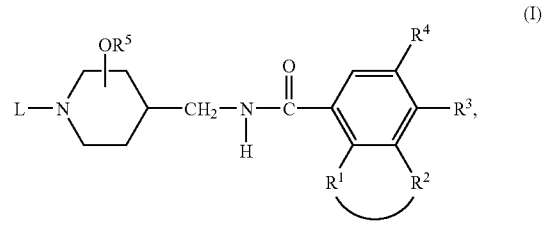

a stereochemically isomeric form thereof, an N-oxide form thereof, or a pharmaceutically acceptable acid or base addition salt thereof, wherein
—R¹—R²— is a bivalent radical of formula —O—CH₂—CH₂—CH₂—O—  (a-5), wherein in said bivalent radicals optionally one or two hydrogen atoms on the same or a different carbon atom may be replaced by $C_{1-6}$alkyl or hydroxy,
R³ is hydrogen, halo, $C_{1-6}$alkyl or $C_{1-6}$alkyloxy;
R⁴ is hydrogen, halo, $C_{1-6}$alkyl; $C_{1-6}$alkyl substituted with cyano, or $C_{1-6}$alkyloxy; $C_{1-6}$alkyloxy; cyano; amino or mono or di($C_{1-6}$alkyl)amino;
R⁵ is hydrogen or $C_{1-6}$alkyl, and the —OR⁵ radical is situated at the 3- or 4-position of the piperidine moiety;
L is a radical of formula -Alk-R⁶  (b-1), -Alk-X—R⁷  (b-2), -Alk-Y—C(=O)—R⁹  (b-3), -Alk-C(=O)—NH—C(=O)—R¹¹  (b-4), -Alk-C(=O)—NH—SO₂—R¹¹  (b-5), -Alk-SO₂—NH—C(=O)—R¹¹  (b-6), -Alk-SO₂—NH—SO₂—R¹¹  (b-7), wherein each Alk is $C_{1-12}$alkanediyl; and
R⁶ is aminosulfonyl optionally substituted with $C_{1-4}$alkyl, $C_{3-6}$cycloalkyl or phenyl;
R⁷ is $C_{1-6}$alkylsulfonyl;
X is NR⁸; said R⁸ being $C_{1-6}$alkyl;
R⁹ is $C_{1-6}$alkylsulfonylamino;
Y is a O, S, or NR¹⁰ wherein R¹⁰ is hydrogen or $C_{1-6}$alkyl; and
R¹¹ is $C_{1-6}$alkyl or phenyl.

2. The compound of claim 1, wherein the —OR⁵ radical is situated at the 3-position of the piperidine moiety having the trans configuration.

3. The compound of claim 2 wherein the absolute configuration of said piperidine moiety is (3S, 4S).

4. The compound of claim 1 wherein L is a radical of formula (b-1) wherein Alk is $C_{1-4}$alkanediyl, and R⁶ aminosulfonyl or aminosulfonyl substituted with $C_{1-4}$alkyl or phenyl.

5. The compound of claim 1 wherein L is a radical (b-5) wherein Alk is $C_{1-4}$alkanediyl, and R¹¹ is $C_{1-4}$alkyl.

6. The compound of claim 1 wherein L is a radical (b-7) wherein Alk is $C_{1-4}$alkanediyl, and R¹¹ is $C_{1-4}$alkyl.

7. A pharmaceutical composition comprising a pharmaceutically acceptable carrier and a therapeutically active amount of a compound according to claim 1.

8. A method for treating hypermotility, irritable bowel syndrome, constipation or diarrhea predominant IBS, pain and non-pain predominant IBS and bowel hypersensitivity comprising administering to a patient in need thereof an effective amount of a compound according to claim 1.

* * * * *